US011210781B2

(12) United States Patent
Xing et al.

(10) Patent No.: US 11,210,781 B2
(45) Date of Patent: Dec. 28, 2021

(54) METHODS AND DEVICES FOR REDUCING DIMENSION OF EIGENVECTORS AND DIAGNOSING MEDICAL IMAGES

(71) Applicant: SHANGHAI UNITED IMAGING INTELLIGENCE CO., LTD., Shanghai (CN)

(72) Inventors: Xiaodan Xing, Shanghai (CN); Feng Shi, Shanghai (CN); Yiqiang Zhan, Shanghai (CN)

(73) Assignee: SHANGHAI UNITED IMAGING INTELLIGENCE CO., LTD., Shanghai (CN)

( * ) Notice: Subject to any disclaimer, the term of this patent is extended or adjusted under 35 U.S.C. 154(b) by 180 days.

(21) Appl. No.: 16/555,716

(22) Filed: Aug. 29, 2019

(65) Prior Publication Data
US 2020/0104984 A1   Apr. 2, 2020

(30) Foreign Application Priority Data
Sep. 29, 2018  (CN) .......................... 201811147961.X

(51) Int. Cl.
   *G06T 7/00*    (2017.01)
   *G06F 17/16*   (2006.01)
   *G16H 50/20*   (2018.01)

(52) U.S. Cl.
   CPC ............ *G06T 7/0012* (2013.01); *G06F 17/16* (2013.01); *G16H 50/20* (2018.01);
   (Continued)

(58) Field of Classification Search
   None
   See application file for complete search history.

(56) References Cited

U.S. PATENT DOCUMENTS

2010/0061609 A1 *  3/2010  Shinagawa ........... G06T 7/0012
                                                  382/131
2013/0322728 A1 * 12/2013  Jacobs .................. A61B 5/055
                                                  382/132

FOREIGN PATENT DOCUMENTS

CN        105335753 A      2/2016
CN        108093406 A      5/2018

OTHER PUBLICATIONS

Horev, I., Yger, F. & Sugiyama, M. Geometry-aware principal component analysis for symmetric positive definite matrices. Mach Learn 106, 493-522 (2017). https://doi.org/10.1007/s10994-016-5605-5 (Year: 2017).*

(Continued)

*Primary Examiner* — Justin P. Misleh
(74) *Attorney, Agent, or Firm* — Faegre Drinker Biddle & Reath LLP

(57) ABSTRACT

Method and system for reducing a number of eigenvectors. For example, a computer-implemented method for reducing a number of eigenvectors, the method comprising: obtaining a plurality of to-be-processed matrices; mapping the plurality of to-be-processed matrices to a space of symmetric positive definite matrices to form a Riemannian manifold corresponding to a Riemannian kernel function; obtaining a kernel-function matrix by using at least a principal component analysis to calculate one or more inner products of the mapped plurality of matrices based on at least the Riemannian kernel function; calculating a first group of eigenvectors of the kernel-function matrix, the first group of eigenvectors including a first number of eigenvectors; and selecting one or more eigenvectors from the first group of eigenvectors to obtain a second group of eigenvectors, the (Continued)

second group of eigenvectors including a second number of eigenvectors; wherein the second number is less than the first number.

20 Claims, 11 Drawing Sheets

(52) U.S. Cl.
CPC ........... *G06T 2207/10088* (2013.01); *G06T 2207/20021* (2013.01); *G06T 2207/30004* (2013.01)

(56) References Cited

OTHER PUBLICATIONS

S. Jayasumana, R. Hartley, M. Salzmann, H. Li and M. Harandi, "Kernel Methods on the Riemannian Manifold of Symmetric Positive Definite Matrices," 2013 IEEE Conference on Computer Vision and Pattern Recognition, 2013, pp. 73-80, doi: 10.1109/CVPR.2013.17. (Year: 2013).*

Chinese Patent Office, Office Action dated Apr. 17, 2020, in Application No. 201811147961.X.

Hongwei et al., "Feather Quill Crease Recognition Method by Combining Manifold Kernel with LPP," *Opto-Electronic Engineering*, vol. 41, No. 2 (Feb. 2014), pp. 47-52.

* cited by examiner

METHODS AND DEVICES FOR REDUCING DIMENSION OF EIGENVECTORS AND DIAGNOSING MEDICAL IMAGES

1. CROSS-REFERENCES TO RELATED APPLICATIONS

This application claims priority to Chinese Patent Application No. 201811147961.X, filed Sep. 29, 2018, incorporated by reference herein for all purposes.

2. BACKGROUND OF THE INVENTION

Certain embodiments of the present invention are directed to information processing. More particularly, some embodiments of the invention provide systems and methods for reducing a number of eigenvectors. Merely by way of example, some embodiments of the invention have been applied to diagnosing a medical image. But it would be recognized that the invention has a much broader range of applicability.

When image processing and other large-scale multi-dimensional matrix data need to be processed, principal component analysis (PCA), also sometimes referred to as the principal weight analysis, may be used for dimension reduction to transform multiple indicators into a few comprehensive indicators. Principal component analysis is a mathematical transformation method that converts a given set of related variables into another set of unrelated variables based on linear transformation. These new variables are arranged in descending order of variance.

However, for nonlinear two-dimensional data samples, the conventional methods ignore the many important structural information existing in the two-dimensional data matrix, and is unable to separate nonlinear data samples, affecting the image processing results.

3. BRIEF SUMMARY OF THE INVENTION

Certain embodiments of the present invention are directed to information processing. More particularly, some embodiments of the invention provide systems and methods for reducing a number of eigenvectors. Merely by way of example, some embodiments of the invention have been applied to diagnosing a medical image. But it would be recognized that the invention has a much broader range of applicability.

In some embodiments, a computer-implemented method for reducing a number of eigenvectors includes: obtaining a plurality of to-be-processed matrices; mapping the plurality of to-be-processed matrices to a space of symmetric positive definite matrices to form a Riemannian manifold corresponding to a Riemannian kernel function; obtaining a kernel-function matrix by using at least a principal component analysis to calculate one or more inner products of the mapped plurality of matrices based on at least the Riemannian kernel function; calculating a first group of eigenvectors of the kernel-function matrix, the first group of eigenvectors including a first number (e.g., only the first number) of eigenvectors; and selecting one or more eigenvectors from the first group of eigenvectors to obtain a second group of eigenvectors, the second group of eigenvectors including a second number (e.g., only the second number) of eigenvectors; wherein the second number is less than the first number.

In some examples, the first group of eigenvectors correspond to a first group of eigenvalues respectively; and the second group of eigenvectors correspond to a second group of eigenvalues respectively.

In some examples, the first group of eigenvalues include a third number (e.g., only the third number) of eigenvalues; and the second group of eigenvalues include a fourth number (e.g., only the fourth number) of eigenvalues; wherein: the third number is equal to the first number; the fourth number is equal to the second number; and the fourth number is less than the third number.

In some examples, the selecting one or more eigenvectors from the first group of eigenvectors to obtain a second group of eigenvectors includes: selecting one or more eigenvectors from the first group of eigenvectors based on at least the first group of eigenvalues.

In some examples, the mapping the plurality of to-be-processed matrices to a space of symmetric positive definite matrices to form a Riemannian manifold corresponding to a Riemannian kernel function includes: transforming the plurality of to-be-processed matrices to a plurality of semi-positive definite Laplacian matrices respectively:

$$L_s = D_s - W_s$$

wherein s is an integer variable ranging from 1 to S, S represents a total number of matrices for the plurality of to-be-processed matrices, $L_s$ represents each of the plurality of semi-positive definite Laplacian matrices, $D_s$ represents a degree matrix of each of the plurality of to-be-processed matrices, and $W_s$ represents each of the plurality of to-be-processed matrices; and regularizing the plurality of semi-positive definite Laplacian matrices into a plurality of symmetric positive definite matrices respectively:

$$\hat{L}_{s,\gamma} = L_s + \gamma I$$

wherein $\hat{L}_{s,\gamma}$ represents each of the plurality of symmetric positive definite matrices, γ represents a positive integer, and I represents an identity matrix.

In some examples, the Riemannian kernel function is represented by:

$$\kappa_{logE}(\hat{L}_{s_1,\gamma}, \hat{L}_{s_2,\gamma}) = \exp\left(-\frac{d_{logE}^2(\hat{L}_{s_1,\gamma}, \hat{L}_{s_2,\gamma})}{\sigma^2}\right),$$

wherein $s_1$ and $s_2$ represent two separate matrices of the plurality of symmetric positive definite matrices.

In some embodiments, a computer-implemented method for diagnosing a medical image includes: obtaining a medical image to be diagnosed; obtaining a plurality of functional correlation matrices based on at least the medical image; mapping the plurality of functional correlation matrices to a space of symmetric positive definite matrices to form a Riemannian manifold corresponding to a Riemannian kernel function; obtaining a kernel-function matrix by using at least a principal component analysis to calculate one or more inner products of the mapped plurality of matrices based on at least the Riemannian kernel function; calculating a first group of eigenvectors of the kernel-function matrix, the first group of eigenvectors including a first number (e.g., only the first number) of eigenvectors; selecting one or more eigenvectors from the first group of eigenvectors to obtain a second group of eigenvectors, the second group of eigenvectors including a second number (e.g., only the second number) of eigenvectors; wherein the second number is less than the first number; and obtaining a diagnostic result associated with the medical image by at least inputting the second group of eigenvectors and a second group of eigenvalues corresponding to the second group of eigenvectors respectively into one or more classifiers.

In some examples, the obtaining a medical image to be diagnosed includes obtaining a functional magnetic resonance image; the obtaining a plurality of functional correlation matrices based on at least the medical image includes: obtaining a plurality of image data by at least performing one or more slice-time corrections, one or more head-motion corrections, one or more normalizations, one or more spatial filterings, and one or more temporal filterings on the medical image; mapping the plurality of image data to multiple regions by at least dividing the plurality of image data into multiple sets of data, the multiple sets of date corresponding to the multiple regions respectively; and obtaining the plurality of functional correlation matrices by at least calculating one or more correlation coefficients between the multiple sets of data.

In some examples, the first group of eigenvectors correspond to a first group of eigenvalues respectively; and the second group of eigenvectors correspond to the second group of eigenvalues respectively.

In some examples, the first group of eigenvalues include a third number (e.g., only the third number) of eigenvalues; and the second group of eigenvalues include a fourth number (e.g., only the fourth number) of eigenvalues; wherein: the third number is equal to the first number; the fourth number is equal to the second number; and the fourth number is less than the third number.

In some examples, the selecting one or more eigenvectors from the first group of eigenvectors to obtain a second group of eigenvectors includes selecting one or more eigenvectors from the first group of eigenvectors based on at least the first group of eigenvalues.

In some examples, the mapping the plurality of to-be-processed matrices to a space of symmetric positive definite matrices to form a Riemannian manifold corresponding to a Riemannian kernel function includes: transforming the plurality of to-be-processed matrices to a plurality of semi-positive definite Laplacian matrices respectively:

$$L_s = D_s - W_s$$

wherein s is an integer variable ranging from 1 to S, S represents a total number of matrices for the plurality of to-be-processed matrices, $L_s$ represents each of the plurality of semi-positive definite Laplacian matrices, $D_s$ represents a degree matrix of each of the plurality of to-be-processed matrices, and $W_s$ represents each of the plurality of to-be-processed matrices; and regularizing the plurality of semi-positive definite Laplacian matrices into a plurality of symmetric positive definite matrices respectively:

$$\hat{L}_{s,\gamma} = L_s + \gamma I$$

wherein $\hat{L}_{s,\gamma}$ represents each of the plurality of symmetric positive definite matrices, γ represents a positive integer, and I represents an identity matrix.

In some examples, wherein the Riemannian kernel function is represented by:

$$K_{logE}(\hat{L}_{s_1,\gamma}, \hat{L}_{s_2,\gamma}) = \exp\left(-\frac{d_{logE}^2(\hat{L}_{s_1,\gamma}, \hat{L}_{s_2,\gamma})}{\sigma^2}\right),$$

wherein $s_1$ and $s_2$ represent two separate matrices of the plurality of symmetric positive definite matrices.

In various embodiments, a non-transitory computer-readable medium with instructions stored thereon, that when executed by a processor, perform the processes including: obtaining a medical image to be diagnosed; obtaining a plurality of functional correlation matrices based on at least the medical image; mapping the plurality of functional correlation matrices to a space of symmetric positive definite matrices to form a Riemannian manifold corresponding to a Riemannian kernel function; obtaining a kernel-function matrix by using at least a principal component analysis to calculate one or more inner products of the mapped plurality of matrices based on at least the Riemannian kernel function; calculating a first group of eigenvectors of the kernel-function matrix, the first group of eigenvectors including a first number of eigenvectors; selecting one or more eigenvectors from the first group of eigenvectors to obtain a second group of eigenvectors, the second group of eigenvectors including a second number of eigenvectors; wherein the second number is less than the first number; and obtaining a diagnostic result associated with the medical image by at least inputting the second group of eigenvectors and a second group of eigenvalues corresponding to the second group of eigenvectors respectively into one or more classifiers.

4. BRIEF DESCRIPTION OF THE DRAWINGS

5. DETAILED DESCRIPTION OF THE INVENTION

Figure 1:
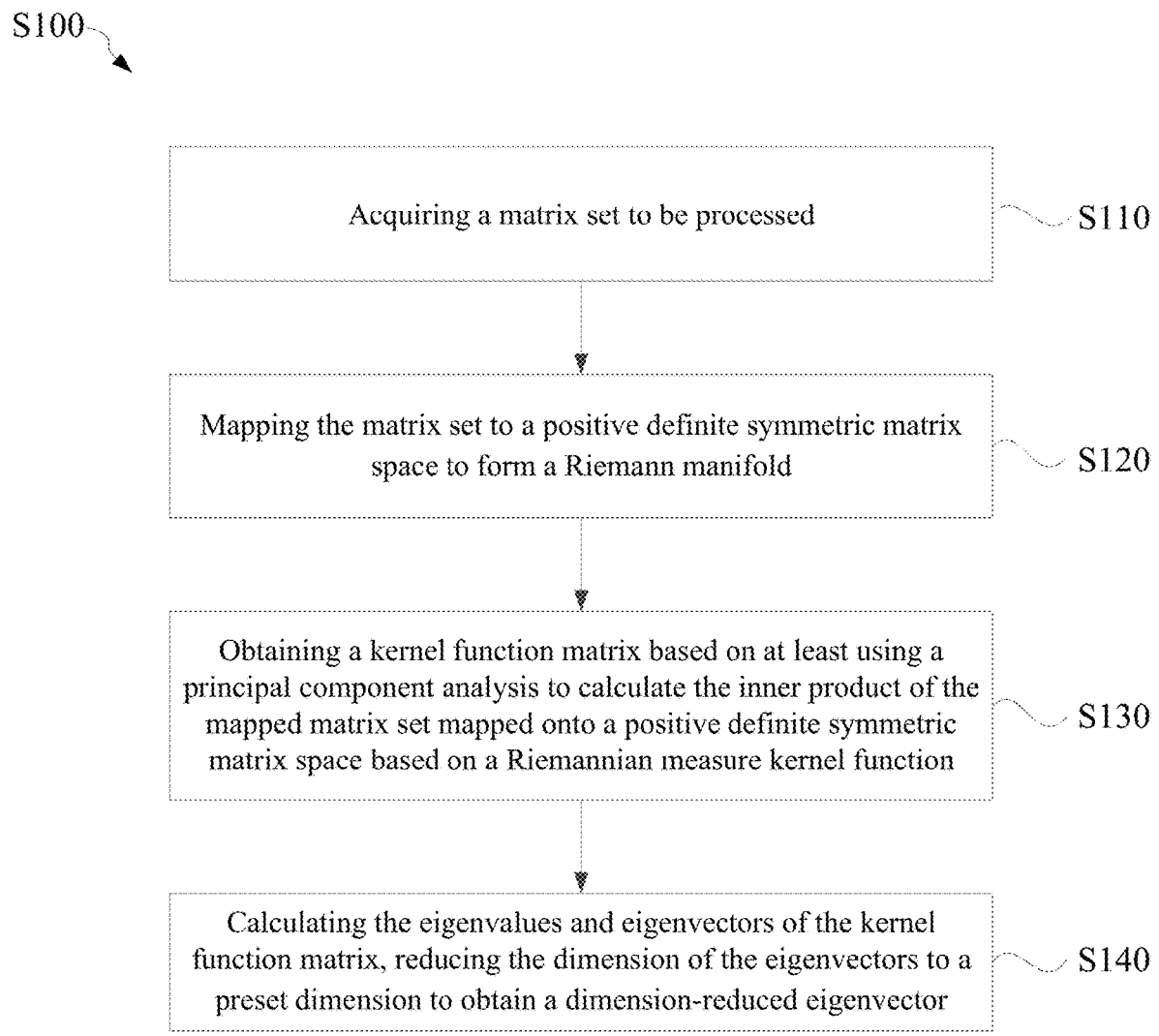
FIG. 1 is a simplified diagram showing a method for eigenvector dimension reduction, according to some embodiments of the present invention.

Certain embodiments of the present invention are directed to information processing. More particularly, some embodiments of the invention provide systems and methods for reducing a number of eigenvectors. Merely by way of example, some embodiments of the invention have been applied to diagnosing a medical image. But it would be recognized that the invention has a much broader range of applicability.

Embodiments of the present invention relate to a medical image analysis technology, and in particular, to an eigenvector dimension reduction method, a medical image recognition method, an apparatus, and/or a storage medium.

In this disclosure, an eigenvector may be referred to as a feature vector, dimension may be referred to as dimensionality, dimension of eigenvectors may be referred to as the number of eigenvectors, correlation may be referred to as connectivity or connection, a classification model may be referred to as a classifier, image may be referred to as image data, mapping may be referred to as projecting, a strong classifier may be referred to as a final classifier, and a recognition result may be referred to as a classification result, a diagnosis result, or a diagnostic result.

In certain embodiments, the disclosed includes an eigenvector dimension (or number) reduction method, a medical image recognition method, an apparatus, and/or a storage medium. In some examples, the eigenvector dimension-reduction method includes acquiring a matrix set to be processed; mapping the matrix set to a positive definite symmetric matrix space to form a Riemann manifold; obtaining a kernel function matrix based on at least using a principal component analysis to calculate the inner product of the mapped matrix set mapped onto a positive definite symmetric matrix space based on a Riemannian measure kernel function; calculating the eigenvalues and eigenvectors of the kernel function matrix, reducing the dimension (e.g., the number) of the eigenvectors to a preset dimension to obtain a dimension-reduced eigenvector. In various embodiments, the disclosed method reduces the dimension of a multidimensional matrix data by using the principal component analysis method and using a Riemannian measure kernel function as a kernel function and can retain important structural information in the matrix data so that the nonlinear data sample features can also be separated, which can be applied to image processing to optimize results.

Embodiments of the present invention provide an eigenvector dimension reduction method, a medical image recognition method, an apparatus, and/or a storage medium, to implement distinguishing features between nonlinear two-dimensional matrix data samples, retain important structural information in data, and optimize data processing results.

In some embodiments, a method for eigenvector dimension-reduction includes: acquiring a matrix set to be processed; mapping the matrix set to a positive definite symmetric matrix space to form a Riemann manifold; obtaining a kernel function matrix based on at least using a principal component analysis to calculate the inner product of the mapped matrix set mapped onto a positive definite symmetric matrix space based on a Riemannian measure kernel function; calculating the eigenvalues and eigenvectors of the kernel function matrix, reducing the dimension (e.g., the number) of the eigenvectors to a preset dimension to obtain dimension-reduced eigenvectors.

In some examples, mapping the matrix set to a positive definite symmetric matrix space to form a Riemannian manifold includes converting the matrix set into a Laplacian matrix with semi-positive definite features based on at least:

$$L_s = D_s - W_s,$$

wherein the matrix set Ws is represented by:

$$\{W_s \in R^{n \times n}, s=1, 2, \ldots, S, w_{ij} \geq 0\},$$

wherein n represents a matrix dimension of the matrix set, S represents the total number of samples, and $D = \text{diag}(\Sigma_j w_{ij})$; and transforming Ls into a positive definite matrix based on at least:

$$\hat{L}_{s,\gamma} = L_s + \gamma I$$

wherein γ represents a positive integer.

In some examples, the Riemann measure kernel function is represented by:

$$\kappa_{logE}(\hat{L}_{s_1,\gamma}, \hat{L}_{s_2,\gamma}) = \exp\left(-\frac{d^2_{logE}(\hat{L}_{s_1,\gamma}, \hat{L}_{s_2,\gamma})}{\sigma^2}\right)$$

wherein $s_1$ and $s_2$ represent two separate matrices of the mapped matrix set for calculating inner product.

In some examples, a medical image recognition method includes obtaining a medical image to be identified and preprocessing the medical image to obtain a functional correlation matrix, and performing a dimension-reduction process on the functional correlation matrix by performing a method for eigenvector dimension-reduction (e.g., the disclosed) to obtain dimension-reduced eigenvectors; and inputting the dimension-reduced eigenvectors into a pre-trained feature classification model to obtain a recognition result.

In some examples, the medical image recognition method further includes: training the feature classification model, and correspondingly, training the feature classification model includes: obtaining abnormal sample image data and normal sample image data, and preprocessing the abnormal sample image data and the normal sample image data to obtain a functional correlation matrix for each sample image data; using an eigenvector dimension-reduction method (e.g., the disclosed) to reduce the dimension of the functional correlation matrix for each sample data to obtain dimension-reduced eigenvectors for each sample data, and generating a training sample set based on the dimension-reduced eigenvectors; inputting the samples of the training sample set into the feature classification model to train, and obtaining a current output recognition result corresponding to each sample; determining whether an error rate between the current output recognition result and an expected output recognition result satisfies a preset condition; and adjusting one or more predicting parameters of the feature classification model if the present condition is not satisfied.

In some examples, the feature classification model to be trained is a base classifier, and the adjusting one or more predicting parameters of the feature classification model includes iterating the base classifier to obtain a plurality of weak classifiers; adjusting the parameters of each weak classifier during the iterating process; and superimposing the base classifier and/or the plurality of weak classifiers to obtain a strong classifier as the feature classification model.

In some examples, preprocessing the medical image to obtain a functional correlation matrix includes performing time registration, motion correction, normalization, and real spatial filtering operations on the medical image to be identified, to obtain first image data; registering and dividing the first image data according to a brain anatomical template (may also be referred to as a functional partition template) to obtain functional partition data; and calculating a correlation coefficient between the data of each functional partition to obtain a correlation matrix.

In some embodiments, an eigenvector dimension-reduction device includes: a matrix obtaining module configured to acquire a matrix set to be processed; a spatial conversion module configured to map the matrix set to a positive definite symmetric matrix space to form a Riemannian manifold; a kernel function acquisition module configured to acquire a kernel function matrix by using a principal component analysis method to calculate an inner product of the matrix set mapped to the positive definite symmetric matrix space based on a Riemann measure kernel function; a dimension-reduction module configured to determine a number of eigenvalues and a number of eigenvectors of the kernel function matrix and reducing the number of eigenvectors to a preset dimension to obtain dimension-reduced eigenvectors.

In some examples, the spatial conversion module is configured to convert the matrix set into a Laplacian matrix with semi-positive definite features based on at least:

$$L_s = D_s - W_s,$$

wherein the matrix set Ws is represented by:

$$\{Ws \in R^{n \times n}, s=1, 2, \ldots, S, w_{ij} \geq 0\},$$

wherein n represents a matrix dimension of the matrix set, S represents the total number of samples, and $D = \text{diag}(\Sigma_j w_{ij})$; and transform Ls into a positive definite matrix based on at least:

$$\hat{L}_{s,\gamma} = L_s + \gamma I,$$

wherein γ represents a positive integer.

In some embodiments, a medical image recognition device includes an image preprocessing module configured to acquire a medical image to be identified and preprocess the medical image to obtain a functional correlation matrix; a dimension-reduction module configured to perform the dimension-reduction method on the functional correlation matrix by using the eigenvector dimension-reduction device to obtain dimension-reduced eigenvector; and an image recognition module configured to input the dimension-reduced eigenvectors into a pre-trained feature classification model to obtain a recognition result.

In some examples, the medical image recognition device further includes a model training module including a data preprocessing unit configured to preprocess the abnormal sample image data and the normal sample image data to obtain a functional correlation matrix for each sample image data; a sample set generating unit configured to generate a training sample set based on the dimension-reduced eigenvectors; a current output recognition resulting unit configured to input the samples of the training sample set into the feature classification model to train, and obtaining a current output recognition result corresponding to each sample; and a parameter adjusting unit configured to determine whether an error rate between the current output recognition result and an expected output recognition result satisfies a preset condition and adjust one or more predicting parameters of the feature classification model if the present condition is not satisfied.

In some examples, the parameter adjusting unit is configured to iterate the base classifier to obtain a plurality of weak classifiers; to adjust the parameters of each weak classifier during the iterating process; and to fuse the base classifier and/or the plurality of weak classifiers to obtain a strong classifier as the feature classification model.

In some examples, the image preprocessing module includes: an image registration and denoising unit configured to perform time registration, motion correction, normalization, and real spatial filtering operations on the medical image to be identified, to obtain first image data; an image division unit configured to register and divide the first image data according to a functional partition template to obtain functional partition data; and a correlation matrix obtaining unit configured to calculate a correlation coefficient between the data of each functional partition to obtain a correlation matrix.

In some embodiments, a server (e.g., a computer) includes one or more processors; a storage device for storing one or more programs; wherein the one or more programs, when executed by the processor, implements the eigenvector dimension-reduction method.

In some embodiments, the server includes one or more processors; a storage device for storing one or more programs; wherein the one or more programs, when executed by the processor, implements the medical image recognition method.

In some embodiments, a computer readable storage medium having stored thereon a computer program, wherein the program, when executed by the processor, implements the eigenvector dimension-reduction method.

In some embodiments, a computer readable storage medium having stored thereon a computer program, wherein the program, when executed by the processor, implements the medical image recognition method.

Embodiments of the present invention reduces the dimension of a multi-dimension matrix data by using a principal component analysis method using a Riemannian measure kernel function as a kernel function, and can retain important structural information in the matrix data, so that nonlinear data sample features can also be separated when applied to image processing, optimizing the results of image processing.

The present invention will be further described in detail below with reference to the accompanying drawings and embodiments. It is understood that the specific embodiments described herein are merely illustrative of the invention and are not intended to limit the invention. It should also be noted that, for ease of description, structures related to the present invention may be shown, added, or removed from the drawings.

FIG. 1 is a simplified diagram showing a method S100 for eigenvector dimension reduction, according to some embodiments (e.g., a first embodiment) of the present invention. This diagram is merely an example, which should not unduly limit the scope of the claims. One of ordinary skill in the art would recognize many variations, alternatives, and modifications. The method may be applied to multi-dimension matrix data processing, such as image processing, which can be performed by an eigenvector dimension-reduction device, which can be configured, for example, in a server. The method S100 includes a process S110 of acquiring a matrix set to be processed, a process S120 of mapping the matrix set to a positive definite symmetric matrix space to form a Riemann manifold, a process S130 of obtaining a kernel function matrix based on at least using a principal component analysis to calculate the inner product of the mapped matrix set mapped onto a positive definite symmetric matrix space based on a Riemannian measure kernel function, and a process S140 of calculating the eigenvalues and eigenvectors of the kernel function matrix, reducing the dimension of the eigenvectors to a preset dimension to obtain a dimension-reduced eigenvector. Although the above has been shown using a selected group of processes for the method, there can be many alternatives, modifications, and variations. For example, some of the processes may be expanded and/or combined. Other processes may be inserted to those noted above. Depending upon the embodiment, the sequence of processes may be interchanged with others replaced.

In various examples, the process S110 of acquiring a matrix set to be processed includes acquiring one or more matrices of experimental data, pixel value matrix data corresponding to pixels in an image, and/or matrix data obtained by mathematically transforming the matrix data. Illustratively, in a medical image such as a magnetic resonance image or a computed tomography (CT) image, the image data is a two-dimension matrix data composed of pixel values of processed voxels. The matrix data in the matrix set can be a nonlinear matrix. In some examples, matrices to be processed are obtained from (e.g., only from) functional MRI and/or diffusion-weighted images. As an example, matrices obtained from functional MRI can be computed from the correlation of blood-oxygenation-level and dependent-level contrast signals among brain regions. As another example, matrices obtained from diffusion-weighted images can be computed from the number of white matter fibers among brain regions.

In various examples, the process S120 of mapping the matrix set to a positive definite symmetric matrix space to form a Riemann manifold includes converting the matrix set into a Laplacian matrix with semi-positive definite features based on at least:

$$L_s = D_s - W_s,$$

wherein the matrix set Ws is represented by:

$$\{W_s \in R^{n \times n}, s=1, 2, \ldots, S, w_{ij} \geq 0\},$$

wherein n represents a matrix dimension of the matrix set, S represents the total number of samples, and $D=\text{diag}(\Sigma_j w_{ij})$; and transforming Ls into a positive definite matrix based on at least:

$$\hat{L}_{s,\gamma} = L_s + \gamma I,$$

wherein $\gamma$ represents a positive integer, and I represents an identity matrix. As an example, for a matrix set including 100 100×100 matrices, the value of n is 100 and the value of s is 100.

In various examples, the process S130 of obtaining a kernel function matrix is based on at least using a principal component analysis to calculate the inner product of the mapped matrix set mapped onto a positive definite symmetric matrix space based on a Riemannian measure kernel function, wherein the Riemann measure kernel function is represented by:

$$\kappa_{logE}(\hat{L}_{s_1,\gamma}, \hat{L}_{s_2,\gamma}) = \exp\left(-\frac{d_{logE}^2(\hat{L}_{s_1,\gamma}, \hat{L}_{s_2,\gamma})}{\sigma^2}\right)$$

wherein $s_1$ and $s_2$ represent two separate matrices of the mapped matrix set for calculating inner product. For example, $s_1$ and $s_2$ represent two separate matrices of the 100 matrices and calculating the inner product of the 100 100×100 matrices based on at least the Riemann measure kernel function obtains a (e.g., one) 100×100 kernel function matrix $K^{100 \times 100}$.

In various examples, the process S140 of calculating the eigenvalues and eigenvectors of the kernel function matrix, reducing the dimension of the eigenvectors to a preset dimension to obtain a dimension-reduced eigenvector. For example, the process S140 includes arranging the eigenvalues $[\lambda_1, \lambda_2, \ldots, \lambda_{100}]$ and their corresponding eigenvectors $[\alpha_1, \alpha_2, \ldots, \alpha_{100}]$ of the kernel function matrix $K^{100 \times 100}$, such as by arranging according to the sizes of the eigenvalues in descending order, wherein the sizes of the eigenvalues represent the amount of information of the original data (e.g., image data of the original image) in the direction of the eigenvectors.

In various examples, reducing the dimension of the eigenvectors to a preset dimension to obtain a dimension-reduced eigenvector includes reducing the dimension of the original data to m-dimension. For example, reducing the dimension of the original data to m-dimension includes selecting the first m number of eigenvectors $[\lambda_1, \lambda_2, \ldots, \lambda_m]$ containing the largest quantity of information, represented by their corresponding eigenvalues $[\alpha_1, \alpha_2, \ldots, \alpha_m]$, in their corresponding directions, mapping the matrix data of the matrix set to a m-dimension low-dimension space, and obtaining coordinates of the mapped matrix data. By this process, the eigenvectors of each sample (e.g., of a sample set) is reduced tom dimensions, wherein m is a value that is set empirically and is smaller than the matrix dimension of the matrix set (e.g., when first acquired, before mapping).

In various examples, the described principal component-based analysis method using a Riemannian measure kernel function as a kernel function is an improvement of a linear principal component-based analysis method. For example, by using a kernel trick, the described method enables nonlinear data samples can also be separated, allowing preserving of the two-dimensional (2D) topology of the original data.

In certain embodiments, an eigenvector dimension-reduction model is established based on at least the eigenvector dimension reduction method described. In certain examples, after determining the parameters of the eigenvector dimension-reduction model, matrix data can be inputted into the eigenvector dimension-reduction model for dimension-reduction.

In some embodiments, the disclosed eigenvector dimension-reduction method based on a principal component analysis method using a Riemann measure kernel function as a kernel function to reduce the dimension of a multidimensional matrix data enables important structural information in the matrix data be retained, and nonlinear data sample features can be separated, when applied to image processing to optimize the image processing results.

Figure 2:
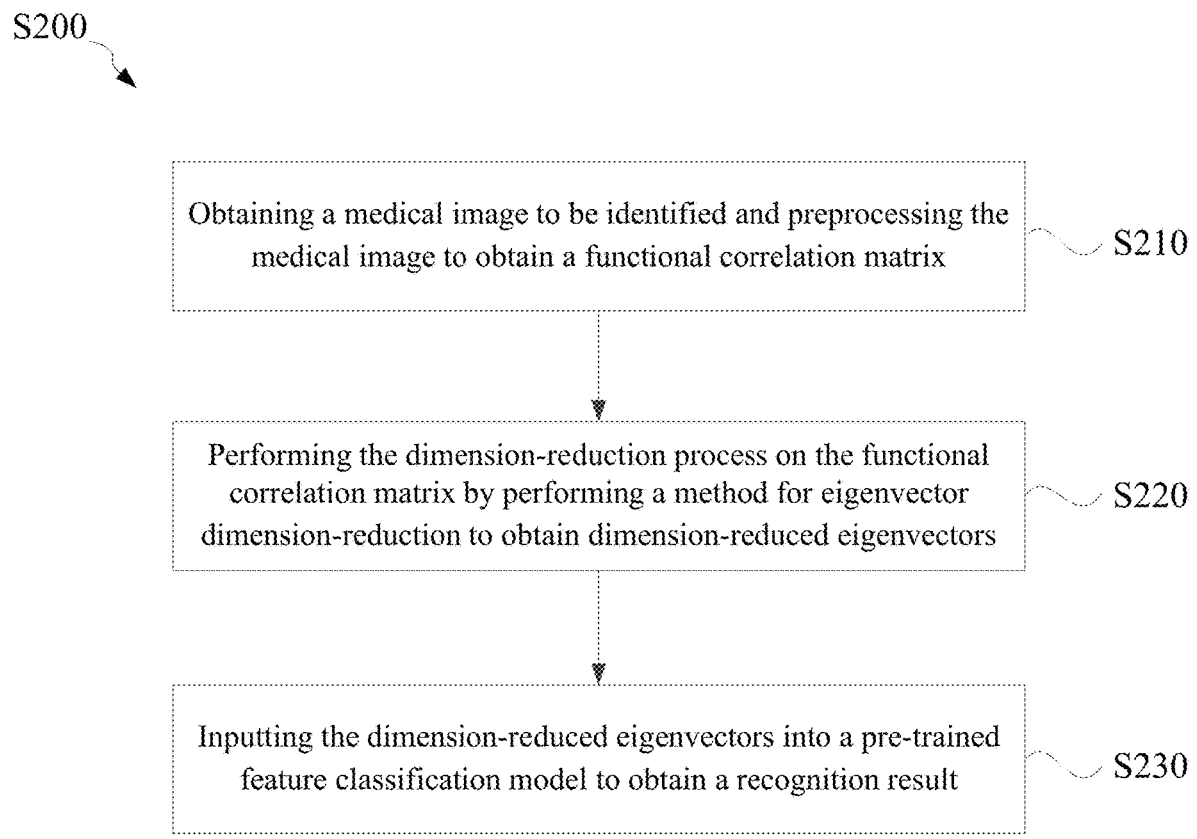
FIG. 2 is a simplified diagram showing a method for medical image recognition, according to some embodiments of the present invention.
Figure 3:
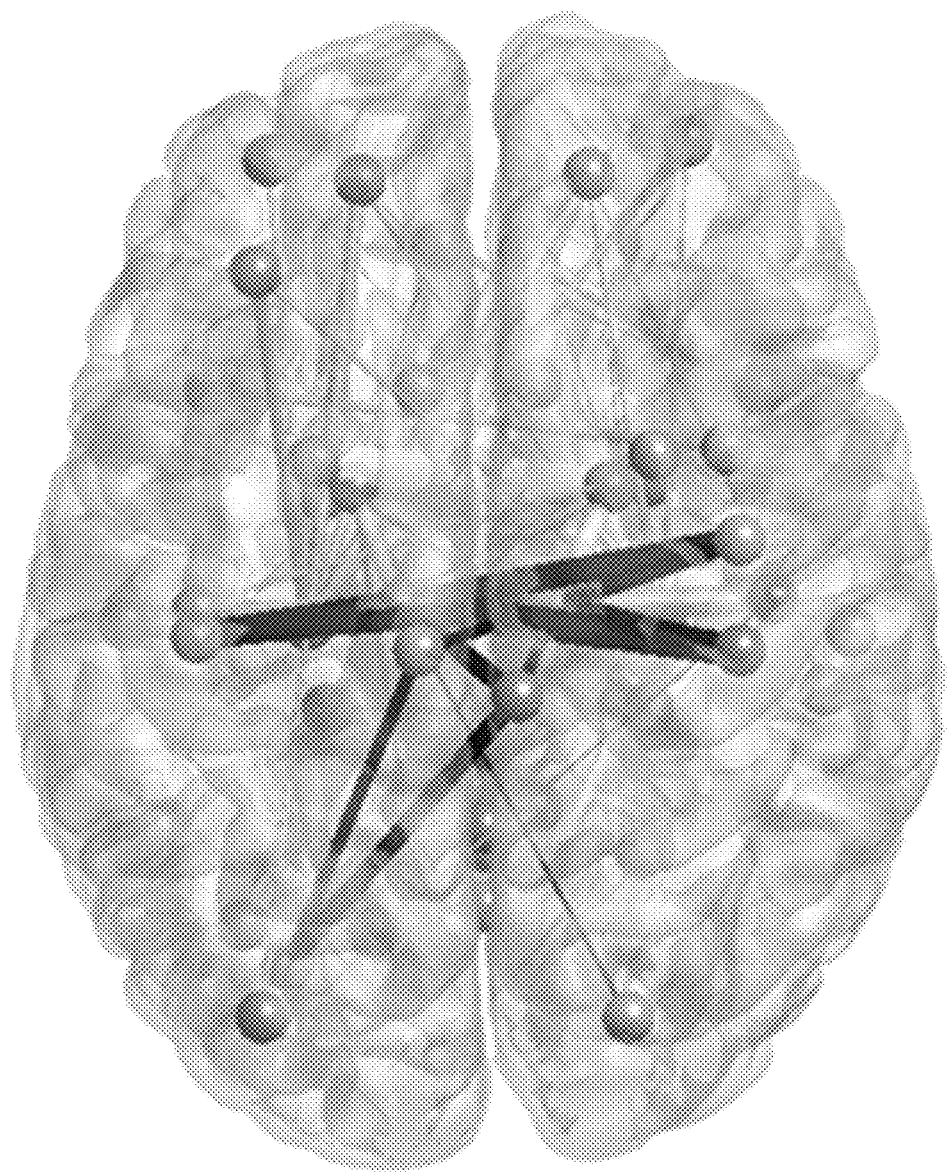
FIG. 3 is a representative view showing, from a coronal planar view, correlated important brain regions in a medical image of a brain of an obsessive-compulsive disorder patient, according to some embodiments of the present invention.
Figure 4:
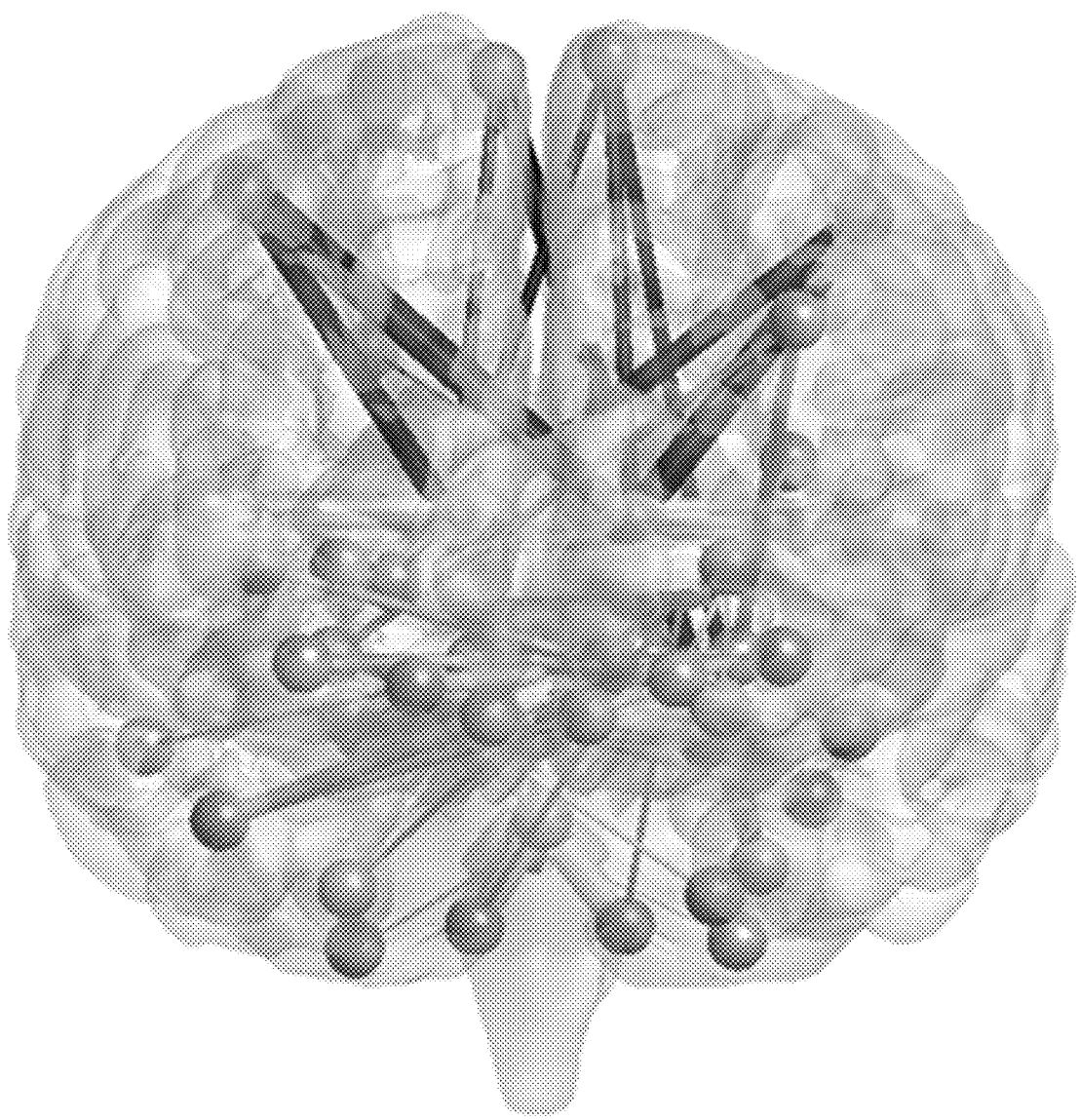
FIG. 4 is a representative view showing, from a cross-sectional planar view, correlated important brain regions in a medical image of a brain of an obsessive-compulsive disorder patient, according to some embodiments of the present invention.
Figure 5:
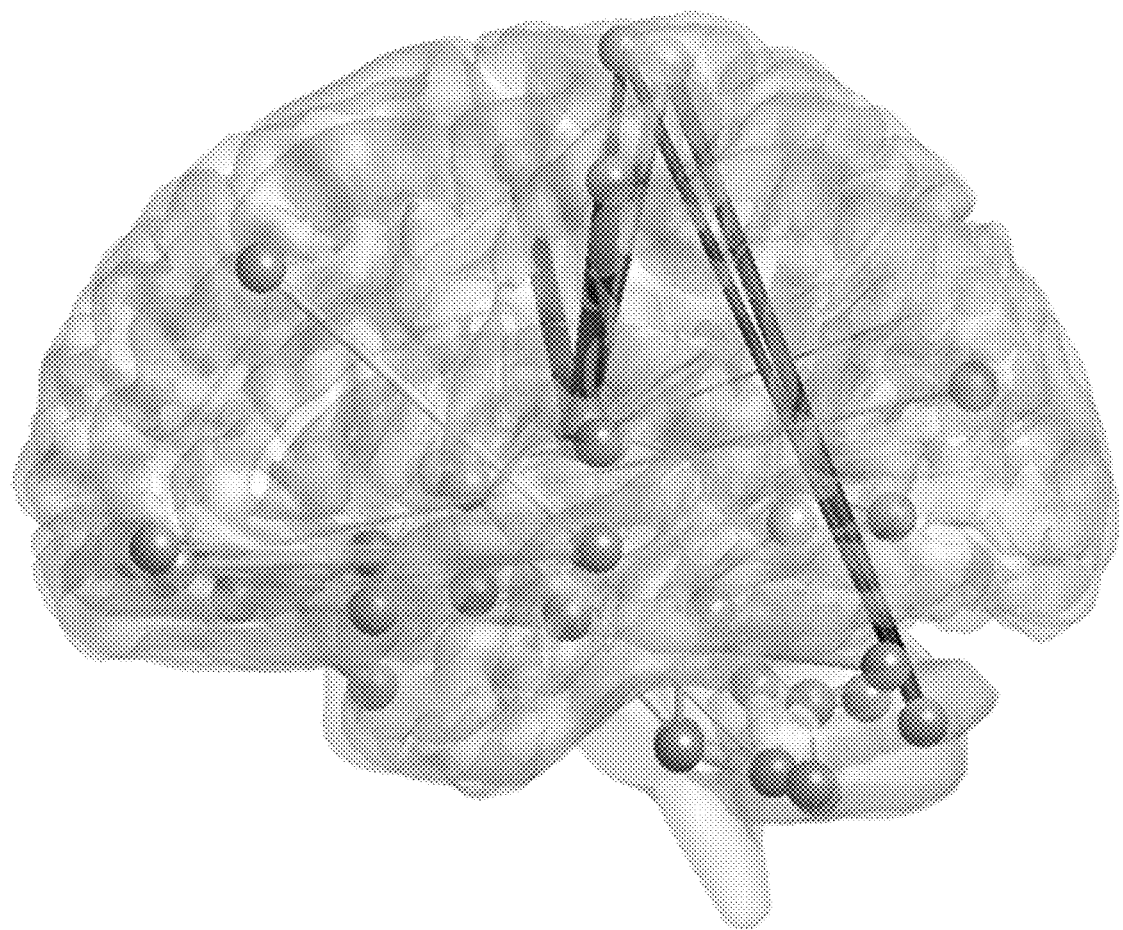
FIG. 5 is a representative view showing, from a Sagittal planar view, correlated important brain regions in a medical image of a brain of an obsessive-compulsive disorder patient, according to some embodiments of the present invention.
Figure 6:
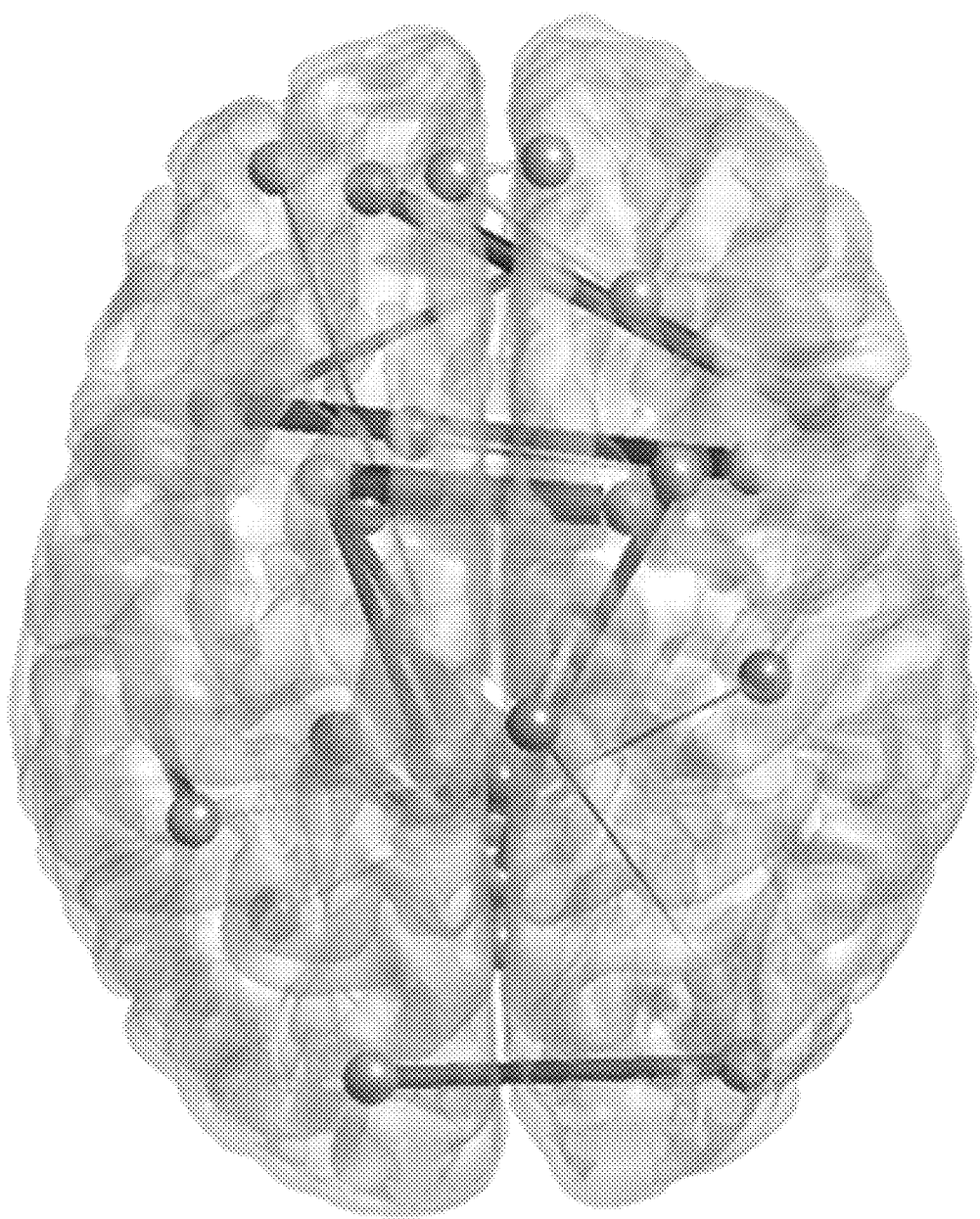
FIG. 6 is a representative view showing a direct visualization of correlated important brain regions in a medical image of a brain of an obsessive-compulsive disorder patient, according to some embodiments of the present invention.

FIG. 2 is a simplified diagram showing a method S200 for medical image recognition, according to some embodiments (e.g., a second embodiment) of the present invention. This diagram is merely an example, which should not unduly limit the scope of the claims. One of ordinary skill in the art would recognize many variations, alternatives, and modifications. In some examples, the method S200 is configured to be implemented based on the described method S100 for eigenvector dimension-reduction. In certain examples, the medical image is subjected to the method S100 for eigenvector dimension-reduction to extract one or more features (e.g., each represented by an eigenvector and a corresponding eigenvalue), which are analyzed against known correlations or connections with strong association or indication with a certain disease. The method S200 includes a process S210 of obtaining a medical image to be identified and preprocessing the medical image to obtain a functional correlation matrix, a process S220 of performing the dimension-reduction process on the functional correlation matrix by performing a method for eigenvector dimension-reduction to obtain dimension-reduced eigenvectors, and a process S230 of inputting the dimension-reduced eigenvectors into a pre-trained feature classification model to obtain a recognition result. Although the above has been shown using a selected group of processes for the method, there can be many alternatives, modifications, and variations. For example, some of the processes may be expanded and/or combined. Other processes may be inserted to those noted above. Depending upon the embodiment, the sequence of processes may be interchanged with others replaced.

In various examples, the process S210 of obtaining a medical image to be identified and preprocessing the medical image to obtain a functional correlation matrix includes obtaining a medical image based on at least scanning a target scanning site by functional magnetic resonance. For example, the medical image is a functional magnetic resonance image of the brain, a functional magnetic resonance image of the heart, or a functional magnetic resonance image of another organ site.

As an example, a brain functional magnetic resonance image is used as a medical image which is obtained in the process S210.

In some examples, after acquiring the functional magnetic resonance image of the brain, the process S210 includes preprocessing the functional magnetic resonance image data of the brain including sequentially subjecting the image data to time registration, head motion correction, normalization, and real spatial filtering operation to reduce the data acquisition errors caused by motion artifacts and physiological features.

In certain embodiments, after preprocessing, including denoising and/or error-compensating, the process S210 includes registering (or matching) and dividing (or segmenting) the preprocessed (e.g., denoised, and error-compensated) image data based on each functional regions of the brain. In certain examples, registering the preprocessed image data includes registering the preprocessed image data based on at least an Anatomical Automatic Labeling (AAL) template. In some examples, dividing the preprocessed image data includes obtaining data of each brain region. In some examples, the AAL template includes 116 regions, wherein 90 regions belong to the brain and 26 regions belong to the cerebellum structure. In various embodiments, each brain region has its corresponding function, and each brain region can work with (e.g., being correlated or connected) one or more other brain regions to achieve a certain function.

In some examples, the process S210 includes, based on the data of each brain region, calculating the average value of the blood oxygen level-dependent (BOLD) signal of all voxels in each brain region, calculating the time series signal between each brain region and other brain regions, and obtaining the correlation coefficient between the time series signals as a functional correlation diagram of the brain regions (e.g., 116 brain regions) of the whole brain, that is, a correlation matrix (e.g., sized 116×116) is obtained. In some examples, the time series signal for each brain region refers to the average of the blood oxygen level dependent (BOLD) signals for all voxels at different times in the brain region.

In various examples, the process S220 of performing the dimension-reduction process on the functional correlation matrix by performing a method for eigenvector dimension-reduction to obtain dimension-reduced eigenvectors is performed based on the method S100, wherein the eigenvector with strong correlation with a target disease is extracted from the correlation matrix without losing image information such as structural information.

In various embodiments, the process S230 of inputting the dimension-reduced eigenvectors into a pre-trained feature classification model to obtain a recognition result includes training the feature classification model, such as using a machine learning process based on a large amount of learning materials. For example, training the feature classification model includes inputting the dimension-reduced eigenvectors obtained by the eigenvector dimension-reduction method into the feature classification model, and outputting a recognition result (or diagnosis result) of the medical image data to be diagnosed according to the input dimension-reduced eigenvectors. In some examples, the learning material includes dimension-reduced eigenvectors obtained by performing the eigenvector dimension-reduction method on a medical image data of a patient having a target disease, and dimension-reduced eigenvectors obtained by performing the eigenvector dimension-reduction method on a medical image data of a normal person without the target disease.

In some examples, after obtaining the classification result, the method S200 further includes reversing the selected features (e.g., represented by eigenvectors and their associated eigenvalues) to obtain (or restore) important one or more original features in the original image by calculating the importance of each feature in the classifier, and visualizing the obtained important one or more original features, which in some examples, can facilitate the interpretation of the results and aid pathological understanding. For example, in the use case of medical image recognition of the brain of an obsessive-compulsive disorder patient, the correlation or connection associated with obsessive-compulsive disorder can be obtained or restored by characteristic reversal. In this use case, the first thirty brain regions that affect a decision tree can be directly displayed on the medical image. The degree of correlation of each brain region is indicated by the identification of different colors in each brain region, thereby indicating the degree of influence of each brain region regarding obsessive-compulsive disorder (e.g., each color represents a degree of correlation). FIGS. 3-6 are representative views showing correlated important brain regions in a medical image of a brain of an obsessive-compulsive disorder patient, from a coronal planar view, a cross-sectional planar view, a Sagittal planar view, and a direct visualization, respectively, according to some embodiments of the present invention. As shown, the higher the grey value (e.g., darker) of a connecting line between the brain regions (e.g., displayed near the center) indicates the higher the strength of the correlation relationship between the connected brain regions. As shown, a connecting line having a higher the grey value corresponds to a thicker connecting line, wherein the thicker the connecting line is, the greater the influence of the correlation between the connected brain functional regions regarding obsessive-compulsive disorder (or a disease of interest). In contrast, the thinner the connecting line, the lesser the influence of the connected brain function regions have on obsessive-compulsive disorder. In some examples, different colors can be used to further distinguish correlation strengths.

In some examples, the method S200 is configured to generate the medical image recognition result to assist the doctor in diagnosing a clinical disease (e.g., obsessive-compulsive disorder) and to improve the diagnosis efficiency.

In various embodiments, a method for reducing the dimension of a medical image data includes using an eigenvector dimension-reduction method, using a Riemann measure kernel function to first increase or boost the dimension of a correlation matrix mapped onto a positive definite symmetric matrix space to a space of higher dimension and following with reducing the dimension of the mapped matrix to a target lower dimension to obtain dimension-reduced eigenvectors, and inputting the dimension-reduced eigenvectors into a pre-trained feature classification model to obtain a recognition result corresponding to the medical image, thereby providing a solution to image processing of a medical image. For example, the described method limits or prevents important information of an image to be lost in the image processing process, which is often the primary cause of low recognition efficiency, reduces image processing time, and improves recognition accuracy.

Figure 7:
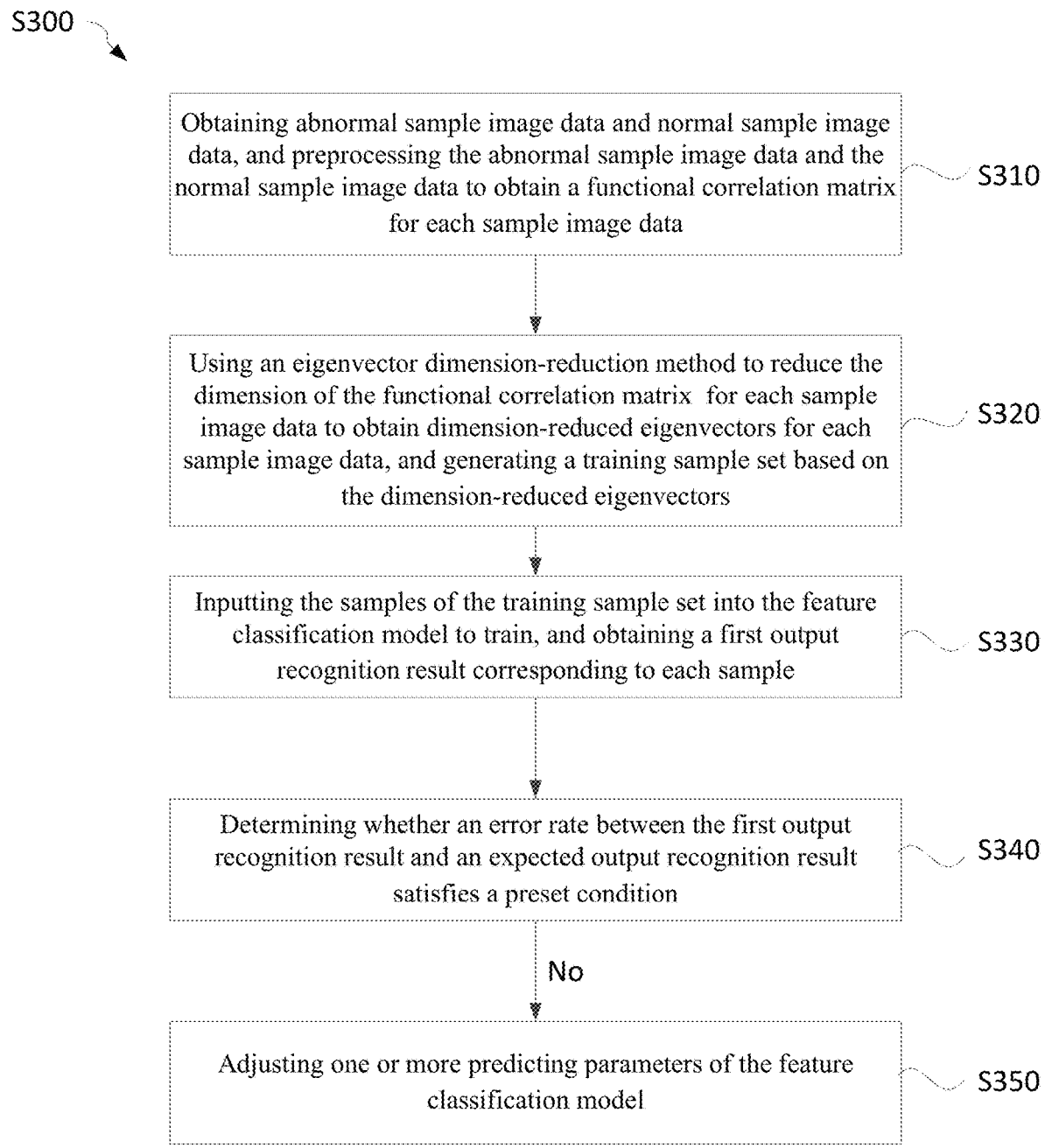
FIG. 7 is a simplified diagram showing a method for training a feature classification model, according to some embodiments of the present invention.

FIG. 7 is a simplified diagram showing a method S300 for training a feature classification model, according to some embodiments (e.g., a third embodiment) of the present invention. This diagram is merely an example, which should not unduly limit the scope of the claims. One of ordinary skill in the art would recognize many variations, alternatives, and modifications. The method S300 may be optimized for the method S200. The method S300 includes a process S310 of obtaining abnormal sample image data and normal sample image data, and preprocessing the abnormal sample image data and the normal sample image data to obtain a functional correlation matrix for each sample image data, a process S320 of using an eigenvector dimension-reduction method to reduce the dimension of the functional correlation matrix for each sample image data to obtain dimension-reduced eigenvectors for each sample image data, and generating a training sample set based on the dimension-reduced eigenvectors, a process S330 of inputting the samples of the training sample set into the feature classification model to train, and obtaining a current output recognition result corresponding to each sample, a process S340 of determining whether an error rate between the current output recognition result and an expected output recognition result satisfies a preset condition, and, if the error rate does not satisfy the preset condition, a process S350 of adjusting one or more predicting parameters of the feature classification model. Although the above has been shown using a selected group of processes for the method, there can be many alternatives, modifications, and variations. For example, some of the processes may be expanded and/or combined. Other processes may be inserted to those noted above. Depending upon the embodiment, the sequence of processes may be interchanged with others replaced.

In various examples, in the process S310 of obtaining abnormal sample image data and normal sample image data and preprocessing the abnormal sample image data and the normal sample image data to obtain a functional correlation matrix for each sample image data, the training samples are selected according to application (e.g., the disease to be diagnosed) of the feature classification model. For example, an abnormal sample is a medical image data of a patient suffering from a certain disease, and a normal sample is a medical image data of a normal person without the disease. In a use case for identifying a medical image to diagnose whether a patient has obsessive-compulsive disorder according to a recognition result, a brain functional magnetic resonance image of the patient suffering from obsessive-compulsive disorder is selected to be an abnormal sample image for training, and a functional magnetic resonance image of the brain of a normal person who does not have obsessive-compulsive disorder is selected to be a normal sample image data for training. In various examples, when a medical image is used to assist in the diagnosis of a target disease (e.g., Parkinson's syndrome), a medical image of a patient suffering from the target disease is selected to be an abnormal sample image for training, and a medical image of a normal person who does not have the target disease is selected to be a normal sample image for training. In various embodiments, the number of abnormal samples and the number of normal samples may be the same value or different values. In certain examples, the higher the number of samples, the higher the accuracy of the recognition result of the trained feature classification model.

In some examples, after preprocessing a medical image, a set of correlation matrices is obtained, and the number of samples corresponds to the size of a dataset. According to the brain function partition of the AAL template, each correlation matrix of the set of correlation matrices is a 116×116 two-dimensional matrix.

In various examples, a S320 of using an eigenvector dimension-reduction method (e.g., method S100) to reduce the dimension of the functional correlation matrix for each sample image data to obtain dimension-reduced (e.g., reduced number of) eigenvectors for each sample image data and generating a training sample set based on the dimension-reduced eigenvectors.

As an example, in a use case with the number of abnormal sample images being sixty-one and the number of normal sample images being sixty-eight, the number of samples in the correlation matrix is one-hundred-twenty-nine, and a kernel function matrix $K^{129 \times 129}$ is obtained via the inner product in the higher-dimension space is based on calculating using a Riemann measure kernel function. Further, the eigenvalues $[\lambda_1, \lambda_2, \ldots, \lambda_{129}]$ of the kernel function matrix $K^{129/129}$ and their corresponding eigenvectors $[\alpha_1, \alpha_2, \ldots, \alpha_{129}]$ are calculated, where the eigenvalues are arranged from high to low, the size of which represents the amount of information of the original data in the direction of their corresponding eigenvector.

In various examples, the process S320 includes reducing the dimension of the eigenvectors to a preset dimension to obtain a dimension-reduced eigenvector includes reducing the dimension of the original data to m-dimension. For example, reducing the dimension of the original data to m-dimension includes selecting the first m number of eigenvectors $[\lambda_1, \lambda_2, \ldots, \lambda_m]$ containing the largest quantity of information, represented by their corresponding eigenvalues $[\alpha_1, \alpha_2, \ldots, \alpha_m]$, in their corresponding directions, mapping the matrix data of the matrix set to a m-dimension low-dimension space, and obtaining coordinates of the mapped matrix data. By this process, the eigenvectors of each sample (e.g., of a sample set) is reduced to m dimensions, wherein m is a value that is set empirically and is smaller than the matrix dimension of the matrix set (e.g., when first acquired, before mapping).

In various examples, the process S330 of inputting the samples of the training sample set into the feature classification model to train and obtaining a current output recognition result corresponding to each sample includes training based on a base classifier (e.g., a basic classifier). For example, the base classifier may be selected from the following classification models including a support vector machine, an over-limit learning machine, a decision tree, a random forest method, a logistic regression, or a ridge regression.

In various examples, the process S340 of determining whether an error rate between the current output recognition result and an expected output recognition result satisfies a preset condition, and, if the error rate does not satisfy the preset condition, performs the process S350.

In various examples, the process S350 of adjusting one or more predicting parameters of the feature classification model. In certain examples, each time a current output recognition result is obtained (e.g., by the base classifier), a weak classifier is obtained. In some examples, a plurality of weak classifiers is iteratively constructed using the base classifier, and a strong classifier is obtained by fusing (or combining) the plurality of weak classifiers and/or their corresponding current output recognition result, the strong classifier being able to generate an output recognition result more accurately and consistently than of a weak classifier. In some examples, the iterating of the plurality of weak classifiers continue if the error rate between the current output recognition result and an expected output recognition result does not satisfy a preset condition (e.g., a threshold confidence value), which may indicate that the current iterated classifier(s) are not satisfactory to be used as a strong (e.g., final) classifier. In various examples, during the iteration process, one or more prediction parameters are continuously adjusted, such as based on the error rate, to help generate the strong classifier.

As an example, in a use case where a regression decision tree model is used as the base classifier, the model is continuously and iterated to generate a regression decision tree. h (x, $\Theta^m$) may represent the $m^{th}$ decision tree, $\Theta^m$ may represent the parameters of the $m^{th}$ decision tree, x may represent the input eigenvector and M is the total number of decision trees. A strong classifier $F_M$ (x) may be generated by linearly adding (or combining) the multiple weak classifiers:

$$F_M(\beta, x) = \sum_{m=1}^{M} \beta_m h(x, \Theta^m)$$

wherein β is the weight of linear addition.

In various examples, every new classifier (e.g., decision tree) generated in the iteration of the plurality of classifiers is generated based on at least the effectiveness of all previously generated classifiers. In some examples, establishing the multiple classifiers iteratively (e.g., regression trees) improves the prediction values (e.g., recognition results) of the tree group continuously to be nearer and nearer to true values (e.g., expected recognition results). In certain examples, each classifier (e.g., decision tree) generated during the iteration is associated with other generated classifier(s), and the input samples for each new classifier are selected based on at least the training results (e.g., recognition results) of the previous classifiers. The relationship is as follows:

$$1 \leq m \leq M \; F_{m+1}(x) = F_m(x) + h(x)$$

In some examples, generating the strong classifier includes obtaining a strong or final model $F_M$ (β, x) configured to generate a recognition result substantially close (e.g., within 30%, 20%, 10%, 5%, or 1% error) to the true result y. In certain examples, generation the strong classifier includes generating a loss function:

$$\Phi(P) = \frac{1}{2}(\gamma - F_M(\beta, x))^2$$

where P refers to all the parameters in the iterative process.

In various examples, the iterative process of generating the strong classifier includes continuously optimizing Φ(P). In such process, based on error of the previous iterations, continuously iterating to generate each new classifier (decision tree) and merging all generated classifiers into a fused classifier (e.g., a decision tree group), correcting any samples that were misclassified (by classifiers of prior iterations) in previous rounds of the iteration process, and obtaining the parameter P which minimizes the loss function in each iteration, until the target prediction accuracy of the training set is obtained. For example, when 100% is reached, the iteration process stops, as the strength of the strong classifier is at its target strength.

In some embodiments, a Boosting method, a method to improve the accuracy of the weak classification algorithm, is used in the iteration process of generating the strong classifier. For example, an XGBoosting (eXtreme Gradient Boosting) algorithm is used, which is an improvement of the Boosting algorithm. As an example, in a use case of diagnosing a medical image to be of a brain of an obsessive-compulsive disorder patient or of a normal human, the regression tree model in the XGBoosting algorithm is used and is shown in FIG. 8.

Figure 8:
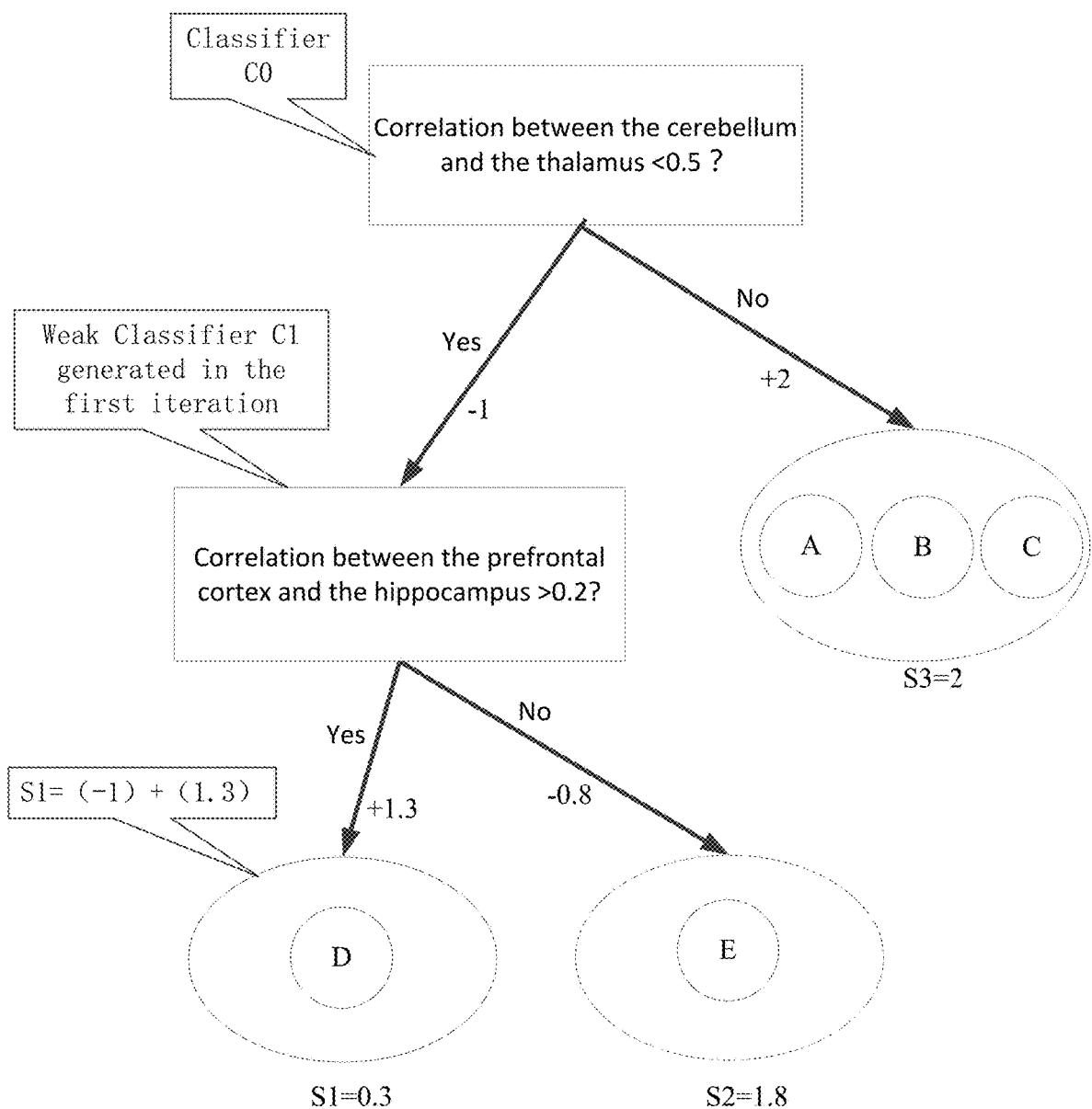
FIG. 8 is a simplified diagram showing a classification tree of an XGBoosting calculating algorithm, according to some embodiments of the present invention.

FIG. 8 is a simplified diagram showing a classification tree of an XGBoosting calculating algorithm, according to some embodiments of the present invention. This diagram is merely an example, which should not unduly limit the scope of the claims. One of ordinary skill in the art would recognize many variations, alternatives, and modifications. For example, the values in the figure, such as S1=0.3, etc., are subject to modification. Although the above has been shown using selected iterative steps, there can be many alternatives, modifications, and variations. For example, some of the steps may be expanded and/or combined. Other steps may be inserted to those noted above. Depending upon the embodiment, the sequence of steps may be interchanged with others replaced.

In the algorithm illustrated in FIG. 8, each rectangular box indicates an iteration or division event of a classifier into the next iteration. In some examples, a sample set is divided into two parts according to the value of the feature, and a series of iterations are generated, wherein the scores of each iteration are added. The sum of the scores of each sample can be calculated, and the sample is judged as an image of the obsessive-compulsive disorder patient based on the sum of the scores. In some examples, a positive score indicates the image is of an obsessive-compulsive disorder patient, and a negative score indicates the image is of a normal person. As an example, the sample D in the FIG. 8 has a correlation between the cerebellum and the thalamus less than 0.5, leading to a score of −1 at the first division event, and has the correlation between the prefrontal cortex and the hippocampus greater than 0.2, leading to a score of +1.3 at the second division event, which leads to a final score of 0.3 that is greater than 0, indicating that the sample D is of a medical image of a normal person without obsessive-compulsive disorder, and the sample E in the dotted ellipse is a medical image of a patient suffering from obsessive-compulsive disorder. Samples A, B, and C were classified as medical images of normal people without OCD after the first iteration (e.g., division event).

In some examples, in the process of iterating the classifiers, a Grid Search method is used to adjust one or more hyperparameters of the classifiers. In a use case when the regression decision tree is used as the base classifier, the hyperparameters to be adjusted may include a learning rate, a minimum leaf node sample weight, a maximum depth of the tree, a maximum step size for each tree weight change, and a threshold for node segmentation determination.

The learning rate may be the step size of each learning (e.g., iteration), similar to the learning rate in a gradient descent method. The minimum leaf node sample weight and the minimum weight of the child nodes generated by the observed sample may be used to prevent over-fitting problems. The threshold of node segmentation judgment may specify the function drop value associated for node splitting, where splitting occurs when the function drop value is larger than the threshold.

In some examples, the grid search method used is a traversal algorithm that traverses all super-parameters and obtains the hyperparameter combination with the most superior performance. In certain examples, many XGBoosting parameters are available for adjustment, and the typical range of parameter values is large, leading to demanding CPU resources when the traversal method is used for calculating all the hyper-parameters for a long time at once. In various examples, a higher learning rate is used in the parameter adjustment since the minimum leaf node sample weight and the maximum depth of the tree are parameters having greater influence on the result of the final model, for example, the minimum leaf node sample weight and the maximum tree depth are preferentially selected by the grid search, first perform a large-scale coarse adjustment, and then perform a small-scale fine adjustment. In some examples, the threshold parameters of the node segmentation determination are adjusted, and the other parameters are fixed to adjust the learning rate.

In some examples, when the number of abnormal sample images and the number of normal sample images are different, the classification evaluation of the feature classification model is given by sensitivity, specificity, and accuracy, which are considered as judging criteria during adjustment of the hyperparameters. The sensitivity may also be referred to as the true positive rate, that is, the probability that an abnormal sample image is recognized an abnormal sample image, wherein the larger the value of the sensitivity, the more sensitive the diagnostic device is; the specificity may also be referred to as the true negative rate, that is, the probability that a normal sample image is recognized as a normal sample image, wherein the larger the value of the specificity, the more conservative and accurate the diagnostic device is; the accuracy is the ratio of the sum of the number of abnormal image data recognized as abnormal and the number of normal sample image data recognized as normal in respect to the number of all samples.

As an example, in the use case of brain image recognition of an obsessive-compulsive disorder patient, a ten-fold (e.g., 10-iteration) verification process generates a final classifier with 90% accuracy, and the operation time of the medical image recognition program (e.g., in a computer device) is 20-30 seconds, showing increased accuracy and reduced time requirement.

In some embodiments, after the final classifier (e.g., the strong classifier) is constructed, important features can be directly extracted from the classifier. For example, if a feature is selected when making important decisions (e.g., at each iteration) according to a decision tree, the selected feature has a higher feature importance. An important characteristic of XGBoosting is the method calculates based on at least judging whether splitting (e.g., iterating) will improve the performance of the classifier. The performance of the classifier may be measured by the Gini coefficient. The Gini coefficient (also known as Gini impurity) is the probability that a randomly selected sample in a subset of samples obtained after classification is faultily classified for a certain feature. In some examples, for each decision tree in the model, the classifier is configured to splits according to all features, and the split samples are divided into two subsets. The Gini coefficient of the split is calculated, and if the split causes the Gini coefficient to decrease, then the feature is considered to be a better classification condition. The importance of the features can help identify the important critical brain regions that are useful for diagnosing the target disease.

In some embodiments, the method for training the feature classification model, which includes inputting the dimension-reduced eigenvectors into a base classifier, continuously iterating the base classifier to obtain a plurality of weak classifiers, fusing the plurality of weak classifiers to obtain a strong classifier, and obtaining an image recognition result. The described method may help alleviate challenges such as inaccurate medical image recognition and low recognition efficiency, and help with preprocessing, network generation, feature selection of a medical image, and automatic processing steps including automatic classification configured to automatically detect medical images of patients with a target disease, such as apart from medical images of normal people without the target disease, thereby increasing accuracy and efficiency.

Figure 9:
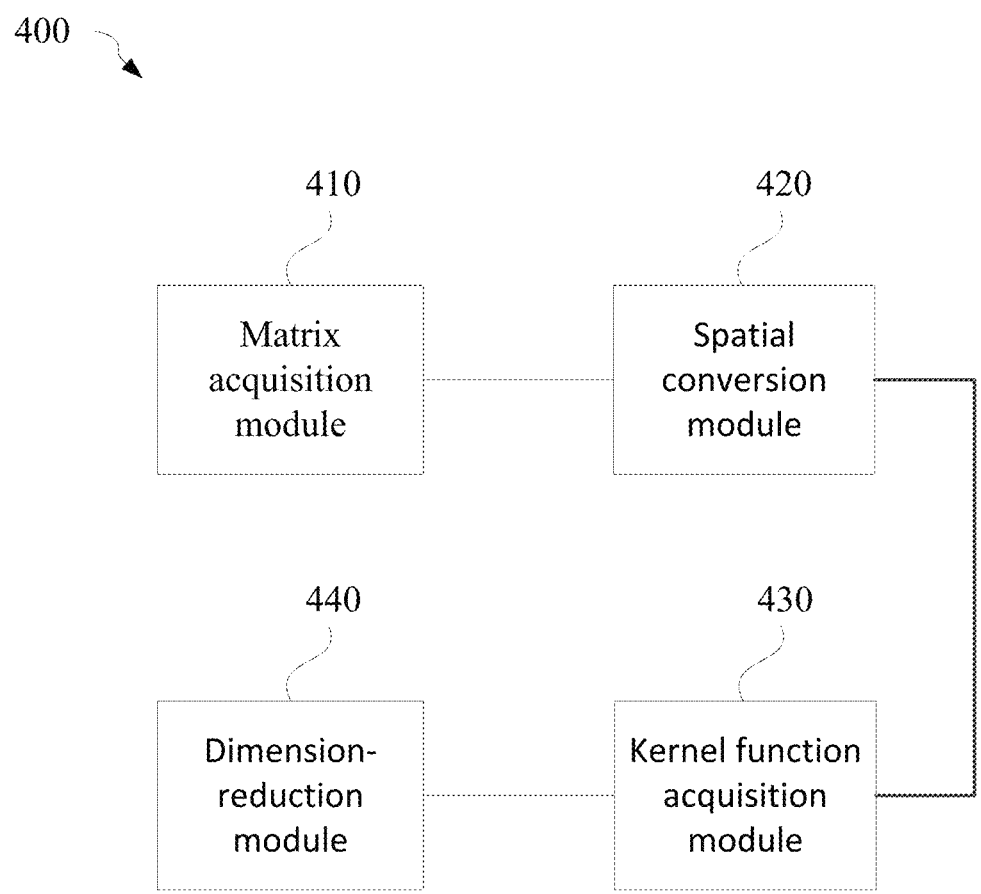
FIG. 9 is a simplified diagram showing an eigenvector dimension-reduction device, according to some embodiments.

FIG. 9 is a simplified diagram showing an eigenvector dimension-reduction device 400, according to some embodiments (e.g., a fourth embodiment). This diagram is merely an example, which should not unduly limit the scope of the claims. One of ordinary skill in the art would recognize many variations, alternatives, and modifications. In some examples, the eigenvector dimension-reduction device 400 is configured to perform the method S100 for eigenvector dimension-reduction. In some examples, the device 400 includes a matrix acquisition module 410, a spatial conversion module 420, a kernel function acquisition module 430, and a dimension-reduction module 440. In certain examples, the matrix acquisition module S410 is configured to perform the process S110, the spatial conversion module 420 is configured to perform the process S120, the kernel function acquisition module 430 is configured to perform the process S130, and/or the dimension-reduction module 440 is configured to perform the process S140. Although the above has been shown using a selected group of components for the system, there can be many alternatives, modifications, and variations. For example, some of the components may be expanded and/or combined. Other components may be inserted to those noted above. Depending upon the embodiment, the arrangement of components may be interchanged with others replaced.

In various embodiments, the matrix acquisition module 410 is configured to acquire a matrix set to be processed; the spatial conversion module 420 is configured to map the matrix set to a positive definite symmetric matrix space to form a Riemannian manifold; the kernel function acquisition module 430 is configured to acquire a kernel function matrix by using a principal component analysis method to calculate an inner product of the matrix set mapped to the positive definite symmetric matrix space based on a Riemann measure kernel function; and the dimension-reduction module 440 is configured to determine a number of eigenvalues and a number of eigenvectors of the kernel function matrix and reducing the number of eigenvectors to a preset dimension to obtain dimension-reduced eigenvectors.

In various embodiments, the disclosed method reduces the dimension of a multidimensional matrix data by using the principal component analysis method and using a Riemannian measure kernel function as a kernel function and can retain important structural information in the matrix data so that the nonlinear data sample features can also be separated, which can be applied to image processing to optimize results.

In some examples, the spatial conversion module 420, which may be referred to as a mapping module, is configured to convert a matrix set into a Laplacian matrix with semi-positive definite features based on at least:

$$L_s = D_s - W_s,$$

wherein the matrix set $W_s$ is represented by:

$$\{W_s \in R^{n \times n}, s=1, 2, \ldots, S, w_{ij} \geq 0\},$$

wherein n represents a matrix dimension of the matrix set, S represents the total number of samples, and $D = \text{diag}(\Sigma_j w_{ij})$; and transform $L_s$ into a positive definite matrix based on at least:

$$\hat{L}_{s,\gamma} = L_s + \gamma I$$

wherein $\gamma$ represents a positive integer.

In some examples, the Riemann measure kernel function is represented by:

$$\kappa_{logE}(\hat{L}_{s_1,\gamma}, \hat{L}_{s_2,\gamma}) = \exp\left(-\frac{d_{logE}^2(\hat{L}_{s_1,\gamma}, \hat{L}_{s_2,\gamma})}{\sigma^2}\right)$$

wherein $s_1$ and $s_2$ represent two separate matrices of the mapped matrix set for calculating inner product.

Figure 10:
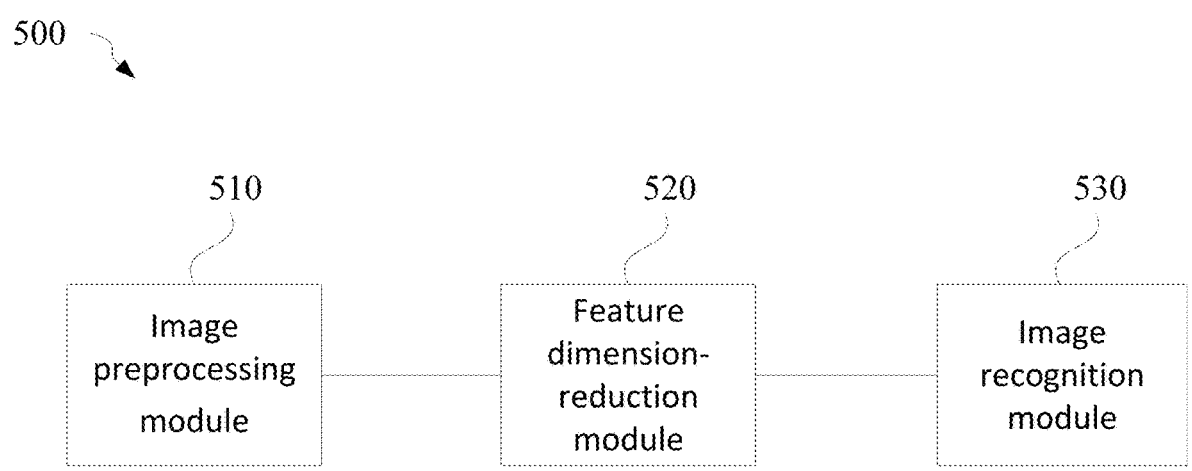
FIG. 10 is a simplified diagram showing a medical image recognition device, according to some embodiments.

FIG. 10 is a simplified diagram showing a medical image recognition device 500, according to some embodiments. This diagram is merely an example, which should not unduly limit the scope of the claims. One of ordinary skill in the art would recognize many variations, alternatives, and modifications. In some examples, the medical image recognition device 400 is configured to perform the method S200 for medical image recognition. In some examples, the device 500 includes an image preprocessing module 510, a dimension-reduction module 520, and an image recognition module 530. In certain examples, the image preprocessing module 510 is configured to perform the process S210, the dimension-reduction module 520 is configured to perform the process S220, and/or the image recognition module 530 is configured to perform the process S230. Although the above has been shown using a selected group of components for the device, there can be many alternatives, modifications, and variations. For example, some of the components may be expanded and/or combined. Other components may be inserted to those noted above. Depending upon the embodiment, the arrangement of components may be interchanged with others replaced.

In some embodiments, the image preprocessing module 510 is configured to acquire a medical image to be identified and preprocess the medical image to obtain a functional correlation matrix; the dimension-reduction module 520 is configured to perform the dimension-reduction method on the functional correlation matrix by using the eigenvector dimension-reduction device to obtain dimension-reduced eigenvector; and the image recognition module 530 is configured to input the dimension-reduced eigenvectors into a pre-trained feature classification model to obtain a recognition result.

In various embodiments, a method for reducing the dimension of a medical image data includes using an eigenvector dimension-reduction method, using a Riemann measure kernel function to first increase or boost the dimension of a correlation matrix mapped onto a positive definite symmetric matrix space to a space of higher dimension and following with reducing the dimension of the mapped matrix to a target lower dimension to obtain dimension-reduced eigenvectors, and inputting the dimension-reduced eigenvectors into a pre-trained feature classification model to obtain a recognition result corresponding to the medical image, thereby providing a solution to image processing of a medical image. For example, the described method limits or prevents important information of an image to be lost in the image processing process, which is often the primary cause of low recognition efficiency, reduces image processing time, and improves recognition accuracy.

In some examples, the medical image recognition device further includes a model training module configured to train a feature classification model, the module including a data preprocessing unit configured to preprocess the abnormal sample image data and the normal sample image data to obtain a functional correlation matrix for each sample image data; a sample set generating unit configured to generate a training sample set based on the dimension-reduced eigenvectors; a current output recognition resulting unit configured to input the samples of the training sample set into the feature classification model to train, and obtaining a current output recognition result corresponding to each sample; and a parameter adjusting unit configured to determine whether an error rate between the current output recognition result and an expected output recognition result satisfies a preset condition and adjust one or more predicting parameters of the feature classification model if the present condition is not satisfied.

In some examples, the parameter adjusting unit is configured to iterate the base classifier to obtain a plurality of weak classifiers; to adjust the parameters of each weak classifier during the iterating process; and to fuse (or combine) the base classifier and/or the plurality of weak classifiers to obtain a strong classifier as the feature classification model.

In some examples, the image preprocessing module includes: an image registration and denoising unit configured to perform time registration, motion correction, normalization, and real spatial filtering operations on the medical image to be identified, to obtain first image data; an image division unit configured to register and divide the first image data according to a functional partition template to obtain functional partition data; and a correlation matrix obtaining unit configured to calculate a correlation coefficient between the data of each functional partition to obtain a correlation matrix.

Figure 11:
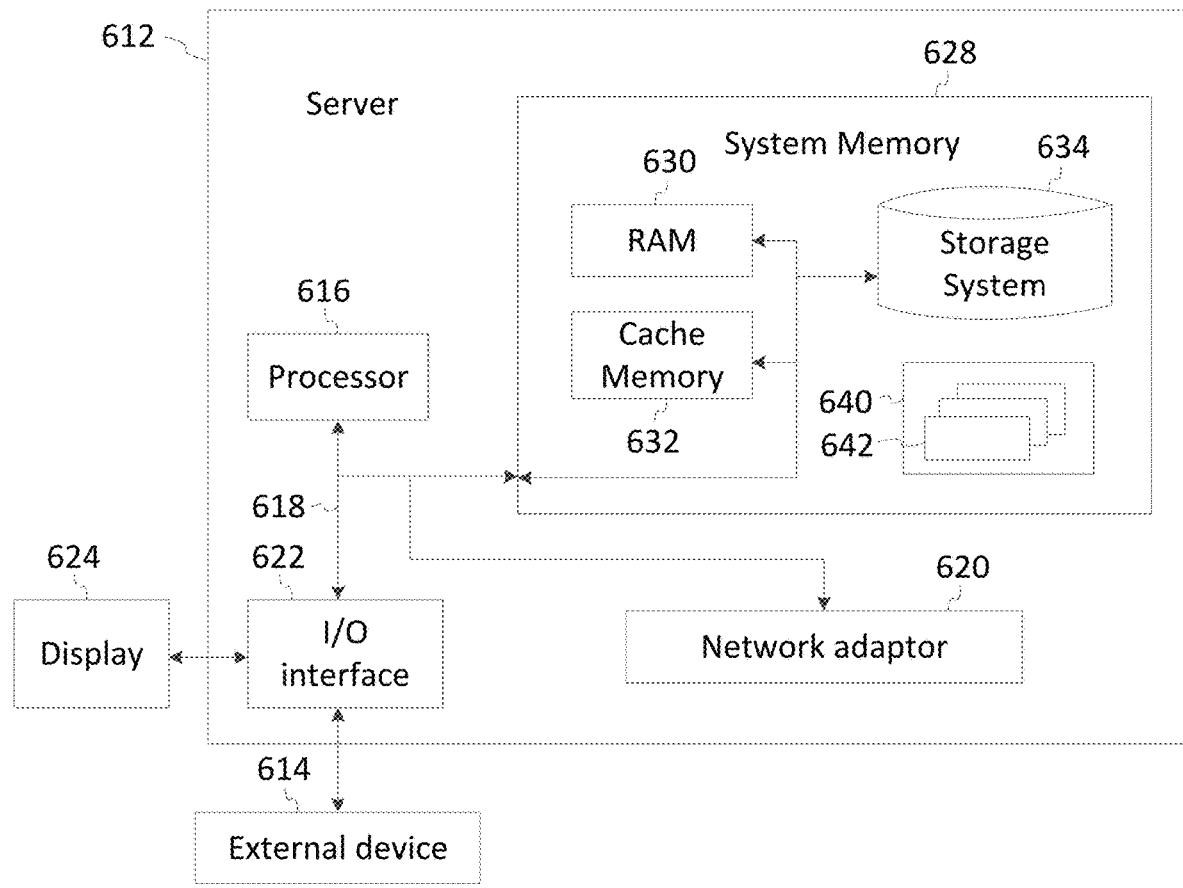
FIG. 11 is a simplified diagram showing a server, according to some embodiments.

FIG. 11 is a simplified diagram showing a server 612, according to some embodiments (e.g., sixth embodiment). This diagram is merely an example, which should not unduly limit the scope of the claims. One of ordinary skill in the art would recognize many variations, alternatives, and modifications. In certain examples, server 612 is a general-purpose computing device. In some examples, the server 612 includes one or more processors or processing units 616, a system memory 628, and a bus 618 that connects various system components including the system memory 628 and the one or more processing units 616. Although the above has been shown using a selected group of components for the server, there can be many alternatives, modifications, and variations. For example, some of the components may be expanded and/or combined. Other components may be inserted to those noted above. Depending upon the embodiment, the arrangement of components may be interchanged with others replaced. In some examples, the server is a computer.

In some examples, some or all processes (e.g., steps) of the method S100 and/or method S200 are performed by a computer device (e.g., server 612). In certain examples, some or all processes (e.g., steps) of the method S100 and/or method S200 are performed by a computer and/or a processor directed by a code. For example, a computer includes a server computer and/or a client computer (e.g., a smartphone). In some examples, some or all processes (e.g., steps) of the S100 and/or method S200 are performed according to instructions included by a non-transitory computer-readable medium (e.g., in a computer program product, such as a mobile app and/or a web app). For example, a non-transitory computer-readable medium is readable by a computer including a server computer and/or a client computer (e.g., a smartphone). As an example, instructions included by a non-transitory computer-readable medium are executed by a processor including a processor of a server computer and/or a processor of a client computer (e.g., a smartphone).

In various examples, the bus 618 represents one or more of several types of bus structures, including a memory bus or a memory controller, a peripheral bus, a graphics acceleration port, a processor, or a local bus using any of a variety of bus structures. For example, these architectures include, but are not limited to, an Industry Standard Architecture (ISA) bus, a Micro Channel Architecture (MAC) bus, an Enhanced ISA Bus, a Video Electronics Standards Association (VESA) local bus, and peripheral component interconnects (PCI) bus.

In some examples, the server 612 includes a variety of computer system readable media. These media can be any available media that can be accessed by server 612, including volatile and non-volatile media, removable and non-removable media.

In various examples, the system memory 628 can include computer system readable media in the form of volatile memory, such as random-access memory (RAM) 630 and/or cache memory 632. In certain examples, the server 612 further includes other removable/non-removable, volatile/non-volatile computer system storage media. Bin some examples, the storage system 634 is used to read and write non-removable, non-volatile magnetic media (not shown), which may be referred to as hard disk drives. In some examples, a disk drive for reading and writing to a removable non-volatile disk (e.g., a floppy disk) and/or a removable non-volatile disk (e.g., CD-ROM, DVD-ROM), and/or another optical media-storing optical drive (e.g., readable and writable) is provided. For example, such additional storage drive is coupled to bus 618 via one or more data medium interfaces. In some examples, the memory 628 includes at least one program (e.g., program product) having a set (e.g., at least one) of program modules configured to perform the functions of various embodiments of the present invention, such as the method for eigenvector dimension-reduction and/or the method for medical image recognition.

In some examples, a program/utility 640 includes a set (e.g., at least one) of program modules 642 stored, in certain examples, in memory 628. As an example, program module 642 includes an operating system, one or more applications, a sub-program module, and/or program data. An implementation of the network environment may be included in each or some of these examples. In some examples, program module 642 includes executable program (e.g., executed by the processor 616) that when executed, performs the functions of various embodiments of the present invention, such as the method for eigenvector dimension-reduction and/or the method for medical image recognition.

In some examples, server 612 is configured to be in communication with one or more external devices 614 (e.g., a keyboard, a pointing device, display 624, etc.), in communication with one or more devices that enables a user to interact with the server 612, and/or in communicate with any networking device (e.g., network card, modem, etc.) that is in communication with one or more other computing devices. For example, such communication takes place via an input/output (I/O) interface 622. In certain examples, server 612 is configured to communicate with one or more networks (e.g., a local area network (LAN), a wide area network (WAN), and/or a public network (e.g., the Internet) through network adapter 620. In such examples, network adapter 620 communicates with other modules of server 612 via bus 618. In some examples, other hardware and/or software modules may be utilized in connection with server 612, including but not limited to: microcode, device drivers, redundant processing units, external disk drive arrays, RAID systems, tape drives, and/or data backup storage systems.

In various embodiments, a non-transitory computer-readable medium with instructions stored thereon, that when executed by a processor, perform the processes including: acquiring a matrix set to be processed; mapping the matrix set to a positive definite symmetric matrix space to form a Riemann manifold; obtaining a kernel function matrix based on at least using a principal component analysis to calculate the inner product of the mapped matrix set mapped onto a positive definite symmetric matrix space based on a Riemannian measure kernel function; calculating the eigenvalues and eigenvectors of the kernel function matrix, reducing the dimension (e.g., the number) of the eigenvectors to a preset dimension to obtain a dimension-reduced eigenvector.

In various embodiments, a non-transitory computer-readable medium with instructions stored thereon, that when executed by a processor, perform the processes including: obtaining a medical image to be identified and preprocessing the medical image to obtain a functional correlation matrix, and performing a dimension-reduction process on the functional correlation matrix by performing a method for eigenvector dimension-reduction (e.g., the disclosed) to obtain dimension-reduced eigenvectors; and inputting the dimension-reduced eigenvectors into a pre-trained feature classification model to obtain a recognition result.

In some examples, the computer storage medium employs any combination of one or more computer readable mediums, wherein the computer readable medium is configured to be a computer readable signal medium or a computer readable storage medium. In certain examples, the computer readable storage medium is based on an electronic, magnetic, optical, electromagnetic, infrared, or semiconductor system, apparatus, or device, or any combination of the above. In various examples, the computer readable storage media includes electrical connections having one or more wires, a portable computer disk, a hard disk, a random access memory (RAM), a read only memory (ROM), erasable programmable read only memory (EPROM or flash memory), optical fiber, portable compact disk read only memory (CD-ROM), optical storage device, magnetic storage device, or any suitable combination of the foregoing. In certain embodiments, a computer readable storage medium can be any tangible medium that can contain or store a program, which can be used by or in connection with an instruction execution system, apparatus or device.

In some examples, a computer readable signal medium includes a data signal that is propagated in the baseband or as part of a carrier, carrying computer readable program code. Such propagated data signals can take a variety of forms including, but not limited to, electromagnetic signals, optical signals, or any suitable combination of the foregoing. The computer readable signal medium can also be any computer readable medium other than a computer readable storage medium, which can transmit, propagate, or transport a program for use by or in connection with the instruction execution system, apparatus, or device.

Program code embodied on a computer readable medium can be transmitted by any suitable medium, including but not limited to wireless, wire, fiber optic cable, RF, etc., or any suitable combination of the foregoing.

Computer program code for performing the operations of the present invention may be written in one or more programming languages, or a combination thereof, including an object-oriented programming language such as Java, Smalltalk, C++, and conventional A procedural programming language—such as a "language" or similar programming language. The program code may execute entirely on the user's computer, partly on the user's computer, as a stand-alone software package, partly on the user's computer, partly on the remote computer, or entirely on the remote computer or server. In the case of a remote computer, the remote computer can be connected to the user's computer through any kind of network, including a local area network (LAN) or wide area network (WAN) domain, or can be connected to an external computer (e.g., using an Internet service provider) Internet connection).

Note that the above are some embodiments of the present invention. Those skilled in the art will appreciate that the present invention is not limited to the specific embodiments described herein, and that various modifications, changes and substitutions may be made without departing from the scope of the invention. The present invention is not limited to the above embodiments, and other equivalent embodiments may be included without departing from the inventive concept. The scope may be determined by the scope of the claims.

In some embodiments, a computer-implemented method for reducing a number of eigenvectors includes: obtaining a plurality of to-be-processed matrices; mapping the plurality of to-be-processed matrices to a space of symmetric positive definite matrices to form a Riemannian manifold corresponding to a Riemannian kernel function; obtaining a kernel-function matrix by using at least a principal component analysis to calculate one or more inner products of the mapped plurality of matrices based on at least the Riemannian kernel function; calculating a first group of eigenvectors of the kernel-function matrix, the first group of eigenvectors including a first number (e.g., only the first number) of eigenvectors; and selecting one or more eigenvectors from the first group of eigenvectors to obtain a second group of eigenvectors, the second group of eigenvectors including a second number (e.g., only the second number) of eigenvectors; wherein the second number is less than the first number. In some examples, the computer-implemented method is implemented according to at least the method S100 of FIG. 1. In certain examples, the computer-implemented method is implemented at least by the device 400 of FIG. 9.

In some examples, the first group of eigenvectors correspond to a first group of eigenvalues respectively; and the second group of eigenvectors correspond to a second group of eigenvalues respectively.

In some examples, the first group of eigenvalues include a third number (e.g., only the third number) of eigenvalues; and the second group of eigenvalues include a fourth number (e.g., only the fourth number) of eigenvalues; wherein: the third number is equal to the first number; the fourth number is equal to the second number; and the fourth number is less than the third number.

In some examples, the selecting one or more eigenvectors from the first group of eigenvectors to obtain a second group of eigenvectors includes: selecting one or more eigenvectors from the first group of eigenvectors based on at least the first group of eigenvalues.

In some examples, the mapping the plurality of to-be-processed matrices to a space of symmetric positive definite matrices to form a Riemannian manifold corresponding to a Riemannian kernel function includes: transforming the plurality of to-be-processed matrices to a plurality of semi-positive definite Laplacian matrices respectively:

$$L_s = D_s - W_s$$

wherein s is an integer variable ranging from 1 to S, S represents a total number of matrices for the plurality of to-be-processed matrices, $L_s$ represents each of the plurality of semi-positive definite Laplacian matrices, $D_s$ represents a degree matrix of each of the plurality of to-be-processed matrices, and $W_s$ represents each of the plurality of to-be-processed matrices; and regularizing the plurality of semi-positive definite Laplacian matrices into a plurality of symmetric positive definite matrices respectively:

$$\hat{L}_{s,\gamma} = L_s + \gamma I$$

wherein $\hat{L}_{s,\gamma}$ represents each of the plurality of symmetric positive definite matrices, $\gamma$ represents a positive integer, and I represents an identity matrix.

In some examples, the Riemannian kernel function is represented by:

$$\kappa_{logE}(\hat{L}_{s_1,\gamma}, \hat{L}_{s_2,\gamma}) = \exp\left(-\frac{d_{logE}^2(\hat{L}_{s_1,\gamma}, \hat{L}_{s_2,\gamma})}{\sigma^2}\right),$$

wherein $s_1$ and $s_2$ represent two separate matrices of the plurality of symmetric positive definite matrices.

In some embodiments, a computer-implemented method for diagnosing a medical image includes: obtaining a medical image to be diagnosed; obtaining a plurality of functional correlation matrices based on at least the medical image; mapping the plurality of functional correlation matrices to a space of symmetric positive definite matrices to form a Riemannian manifold corresponding to a Riemannian kernel function; obtaining a kernel-function matrix by using at least a principal component analysis to calculate one or more inner products of the mapped plurality of matrices based on at least the Riemannian kernel function; calculating a first group of eigenvectors of the kernel-function matrix, the first group of eigenvectors including a first number (e.g., only the first number) of eigenvectors; selecting one or more eigenvectors from the first group of eigenvectors to obtain a second group of eigenvectors, the second group of eigenvectors including a second number (e.g., only the second number) of eigenvectors; wherein the second number is less than the first number; and obtaining a diagnostic result associated with the medical image by at least inputting the second group of eigenvectors and a second group of eigenvalues corresponding to the second group of eigenvectors respectively into one or more classifiers. In some examples, the computer-implemented method is implemented according to at least the method S200 of FIG. 2. In certain examples, the computer-implemented method is implemented at least by the device 500 of FIG. 10.

In some examples, the obtaining a medical image to be diagnosed includes obtaining a functional magnetic resonance image; the obtaining a plurality of functional correlation matrices based on at least the medical image includes: obtaining a plurality of image data by at least performing one or more slice-time corrections, one or more head-motion corrections, one or more normalizations, one or more spatial filterings, and one or more temporal filterings on the medical image; mapping the plurality of image data to multiple regions by at least dividing the plurality of image data into multiple sets of data, the multiple sets of date corresponding to the multiple regions respectively; and obtaining the plurality of functional correlation matrices by at least calculating one or more correlation coefficients between the multiple sets of data.

In some embodiments, a system for reducing a number of eigenvectors includes: a matrix obtaining module configured to obtain a plurality of to-be-processed matrices; a mapping module configured to map the plurality of to-be-processed matrices to a space of symmetric positive definite matrices to form a Riemannian manifold corresponding to a Riemannian kernel function; a kernel-function matrix obtaining module configured to obtain a kernel-function matrix by using at least a principal component analysis to calculate one or more inner products of the mapped plurality of matrices based on at least the Riemannian kernel function; and a dimension-reducing module configured to: calculate a first group of eigenvectors of the kernel-function matrix, the first group of eigenvectors including a first number (e.g., only the first number) of eigenvectors; and select one or more eigenvectors from the first group of eigenvectors to obtain a second group of eigenvectors, the second group of eigenvectors including a second number (e.g., only the second number) of eigenvectors; wherein the second number is less than the first number. In some examples, the system is implemented according to at least the system 400 of FIG. 9.

In some examples, the first group of eigenvectors correspond to a first group of eigenvalues respectively; and the second group of eigenvectors correspond to a second group of eigenvalues respectively.

In some examples, the first group of eigenvalues include a third number (e.g., only the third number) of eigenvalues; and the second group of eigenvalues include a fourth number (e.g., only the fourth number) of eigenvalues; wherein: the third number is equal to the first number; the fourth number is equal to the second number; and the fourth number is less than the third number.

In some examples, the dimension-reducing module is further configured to select one or more eigenvectors from the first group of eigenvectors based on at least the first group of eigenvalues to obtain a second group of eigenvectors.

In some embodiments, a system for diagnosing a medical image includes: an image preprocessing module configured to: obtain a medical image to be diagnosed; obtain a plurality of functional correlation matrices based on at least the medical image; a dimension-reduction module configured to: map the plurality of functional correlation matrices to a space of symmetric positive definite matrices to form a Riemannian manifold corresponding to a Riemannian kernel function; obtain a kernel-function matrix by using at least a principal component analysis to calculate one or more inner products of the mapped plurality of matrices based on at least the Riemannian kernel function; calculate a first group of eigenvectors of the kernel-function matrix, the first group of eigenvectors including a first number (e.g., only the first number) of eigenvectors; select one or more eigenvectors from the first group of eigenvectors to obtain a second group of eigenvectors, the second group of eigenvectors including a second number (e.g., only the second number) of eigenvectors; wherein the second number is less than the first number; and an image classification module configured to obtain a diagnostic result associated with the medical image by at least inputting the second group of eigenvectors and a second group of eigenvalues corresponding to the second group of eigenvectors respectively into one or more classifiers. In some examples, the system is implemented according to at least the system 500 of FIG. 10.

In some examples, the first group of eigenvectors correspond to a first group of eigenvalues respectively: and the second group of eigenvectors correspond to a second group of eigenvalues respectively.

In some examples, the first group of eigenvalues include a third number (e.g., only the third number) of eigenvalues; and the second group of eigenvalues include a fourth number (e.g., only the fourth number) of eigenvalues; wherein: the third number is equal to the first number; the fourth number is equal to the second number; and the fourth number is less than the third number.

In some examples, the dimension-reduction module is further configured to select one or more eigenvectors from the first group of eigenvectors based on at least the first group of eigenvalues to obtain a second group of eigenvectors.

In some embodiments, a non-transitory computer-readable medium with instructions stored thereon, that when executed by a processor, perform the processes including: obtaining a medical image to be diagnosed; obtaining a plurality of functional correlation matrices based on at least the medical image; mapping the plurality of functional correlation matrices to a space of symmetric positive definite matrices to form a Riemannian manifold corresponding to a Riemannian kernel function; obtaining a kernel-function matrix by using at least a principal component analysis to calculate one or more inner products of the mapped plurality of matrices based on at least the Riemannian kernel function; calculating a first group of eigenvectors of the kernel-function matrix, the first group of eigenvectors including a first number (e.g., only the first number) of eigenvectors; selecting one or more eigenvectors from the first group of eigenvectors to obtain a second group of eigenvectors, the second group of eigenvectors including a second number (e.g., only the second number) of eigenvectors; wherein the second number is less than the first number; and obtaining a diagnostic result associated with the medical image by at least inputting the second group of eigenvectors and a second group of eigenvalues corresponding to the second group of eigenvectors respectively into one or more classifiers. In some examples, the non-transitory computer-readable medium with instructions stored thereon is implemented according to at least the method S100 of FIG. 1 and/or the server 612 of FIG. 11.

In some examples, the first group of eigenvectors correspond to a first group of eigenvalues respectively and the second group of eigenvectors correspond to a second group of eigenvalues respectively.

In some examples, the first group of eigenvalues include a third number (e.g., only the third number) of eigenvalues; and the second group of eigenvalues include a fourth number (e.g., only the fourth number) of eigenvalues; wherein:

the third number is equal to the first number; the fourth number is equal to the second number; and the fourth number is less than the third number.

In some examples, the non-transitory computer-readable medium, when executed by a processor, further perform the process of selecting one or more eigenvectors from the first group of eigenvectors based on at least the first group of eigenvalues to obtain a second group of eigenvectors.

In some embodiments, a computer-implemented method for training one or more classifiers includes: obtaining a first plurality of abnormal sample images, each sample image of the first plurality of abnormal sample images corresponding to a first known classification; obtaining a second plurality of normal sample images, each sample image of the second plurality of normal sample images corresponding to a second known classification; for each sample image of the first plurality of abnormal sample images and the second plurality of normal sample images: obtaining a plurality of functional correlation matrices based on at least the sample image; mapping the plurality of functional correlation matrices to a space of symmetric positive definite matrices to form a Riemannian manifold corresponding to a Riemannian kernel function; obtaining a kernel-function matrix by using at least a principal component analysis to calculate one or more inner products of the mapped plurality of matrices based on at least the Riemannian kernel function; calculating a first group of eigenvectors of the kernel-function matrix, the first group of eigenvectors including a first number (e.g., only the first number) of eigenvectors; selecting one or more eigenvectors from the first group of eigenvectors to obtain a second group of eigenvectors, the second group of eigenvectors including a second number (e.g., only the second number) of eigenvectors; the second number being less than the first number; and obtaining a diagnostic result associated with the medical image by at least inputting the second group of eigenvectors and a second group of eigenvalues corresponding to the second group of eigenvectors respectively into one or more classifiers; determining one or more error rates by at least comparing the diagnostic result associated with each sample image of the first plurality of abnormal sample images with the first known classification and comparing the diagnostic result associated with each sample image of the second plurality of normal sample images with the second known classification; determining whether the one or more error rates satisfy one or more predetermined conditions; and adjusting one or more predicting parameters of the one or more classifiers if the one or more error rates are determined not to satisfy the one or more predetermined conditions, the one or more classifiers corresponding to a trained feature classification model. In some examples, the method is implemented according to at least the method S300 of FIG. 7.

In some examples, adjusting one or more predicting parameters of the one or more classifiers if the one or more error rates are determined not to satisfy one or more predetermined conditions includes: iterating a base classifier associated with the trained feature classification model to obtain a plurality of weak classifiers, the iterating a base classifier includes: adjusting one or more predicting parameters associated with the plurality of weak classifiers; and obtaining a strong classifier as the trained feature classification model by integrating the plurality of weak classifiers.

In various embodiments, a non-transitory computer-readable medium with instructions stored thereon, that when executed by a processor, perform the processes including: obtaining a medical image to be diagnosed; obtaining a plurality of functional correlation matrices based on at least the medical image; mapping the plurality of functional correlation matrices to a space of symmetric positive definite matrices to form a Riemannian manifold corresponding to a Riemannian kernel function; obtaining a kernel-function matrix by using at least a principal component analysis to calculate one or more inner products of the mapped plurality of matrices based on at least the Riemannian kernel function; calculating a first group of eigenvectors of the kernel-function matrix, the first group of eigenvectors including a first number of eigenvectors; selecting one or more eigenvectors from the first group of eigenvectors to obtain a second group of eigenvectors, the second group of eigenvectors including a second number of eigenvectors; wherein the second number is less than the first number; and obtaining a diagnostic result associated with the medical image by at least inputting the second group of eigenvectors and a second group of eigenvalues corresponding to the second group of eigenvectors respectively into one or more classifiers.

For example, some or all components of various embodiments of the present invention each are, individually and/or in combination with at least another component, implemented using one or more software components, one or more hardware components, and/or one or more combinations of software and hardware components. In another example, some or all components of various embodiments of the present invention each are, individually and/or in combination with at least another component, implemented in one or more circuits, such as one or more analog circuits and/or one or more digital circuits. In yet another example, while the embodiments described above refer to particular features, the scope of the present invention also includes embodiments having different combinations of features and embodiments that do not include all of the described features. In yet another example, various embodiments and/or examples of the present invention can be combined.

Additionally, the methods and systems described herein may be implemented on many different types of processing devices by program code comprising program instructions that are executable by the device processing subsystem. The software program instructions may include source code, object code, machine code, or any other stored data that is operable to cause a processing system to perform the methods and operations described herein. Other implementations may also be used, however, such as firmware or even appropriately designed hardware configured to perform the methods and systems described herein.

The systems' and methods' data (e.g., associations, mappings, data input, data output, intermediate data results, final data results, etc.) may be stored and implemented in one or more different types of computer-implemented data stores, such as different types of storage devices and programming constructs (e.g., RAM, ROM, EEPROM, Flash memory, flat files, databases, programming data structures, programming variables, IF-THEN (or similar type) statement constructs, application programming interface, etc.). It is noted that data structures describe formats for use in organizing and storing data in databases, programs, memory, or other computer-readable media for use by a computer program.

The systems and methods may be provided on many different types of computer-readable media including computer storage mechanisms (e.g., CD-ROM, diskette, RAM, flash memory, computer's hard drive, DVD, etc.) that contain instructions (e.g., software) for use in execution by a processor to perform the methods' operations and implement the systems described herein. The computer components, software modules, functions, data stores and data structures described herein may be connected directly or indirectly to each other in order to allow the flow of data needed for their operations. It is also noted that a module or processor includes a unit of code that performs a software operation, and can be implemented for example as a subroutine unit of code, or as a software function unit of code, or as an object (as in an object-oriented paradigm), or as an applet, or in a computer script language, or as another type of computer code. The software components and/or functionality may be located on a single computer or distributed across multiple computers depending upon the situation at hand.

The computing system can include client devices and servers. A client device and server are generally remote from each other and typically interact through a communication network. The relationship of client device and server arises by virtue of computer programs running on the respective computers and having a client device-server relationship to each other.

This specification contains many specifics for particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations, one or more features from a combination can in some cases be removed from the combination, and a combination may, for example, be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Although specific embodiments of the present invention have been described, it will be understood by those of skill in the art that there are other embodiments that are equivalent to the described embodiments. Accordingly, it is to be understood that the invention is not to be limited by the specific illustrated embodiments.

What is claimed is:

1. A computer-implemented method for diagnosing a medical image, the method comprising:
   obtaining a plurality of to-be-processed matrices based on at least the medical image;
   mapping the plurality of to-be-processed matrices to a space of symmetric positive definite matrices to form a Riemannian manifold corresponding to a Riemannian kernel function;
   obtaining a kernel-function matrix by using at least a principal component analysis to calculate one or more inner products of the mapped plurality of matrices based on at least the Riemannian kernel function;
   calculating a first group of eigenvectors of the kernel-function matrix, the first group of eigenvectors including a first number of eigenvectors;
   selecting one or more eigenvectors from the first group of eigenvectors to obtain a second group of eigenvectors, the second group of eigenvectors including a second number of eigenvectors;
   wherein the second number is less than the first number;
   inputting the second group of eigenvectors into one or more classifiers; and
   generating a diagnostic result associated with the medical image by the one or more classifiers.

2. The computer-implemented method of claim 1, wherein:
   the first group of eigenvectors correspond to a first group of eigenvalues respectively; and
   the second group of eigenvectors correspond to a second group of eigenvalues respectively.

3. The computer-implemented method of claim 2, wherein:
   the first group of eigenvalues include a third number of eigenvalues; and
   the second group of eigenvalues include a fourth number of eigenvalues;
   wherein:
      the third number is equal to the first number;
      the fourth number is equal to the second number; and
      the fourth number is less than the third number.

4. The computer-implemented method of claim 2, wherein the selecting one or more eigenvectors from the first group of eigenvectors to obtain a second group of eigenvectors includes:
   selecting one or more eigenvectors from the first group of eigenvectors based on at least the first group of eigenvalues.

5. The computer-implemented method of claim 1, wherein the mapping the plurality of to-be-processed matrices to a space of symmetric positive definite matrices to form a Riemannian manifold corresponding to a Riemannian kernel function includes:
   transforming the plurality of to-be-processed matrices to a plurality of semi-positive definite Laplacian matrices respectively:

$$L_s = D_s - W_s$$

wherein s is an integer variable ranging from 1 to S, S represents a total number of matrices for the plurality of to-be-processed matrices, $L_s$ represents each of the plurality of semi-positive definite Laplacian matrices, $D_s$ represents a degree matrix of each of the plurality of to-be-processed matrices, and $W_s$ represents each of the plurality of to-be-processed matrices; and
   regularizing the plurality of semi-positive definite Laplacian matrices into a plurality of symmetric positive definite matrices respectively:

$$\hat{L}_{s,\gamma} = L_s + \gamma I$$

wherein $\hat{L}_{s,\gamma}$ represents each of the plurality of symmetric positive definite matrices, γ represents a positive integer, and I represents an identity matrix.

6. The method of claim 5, wherein the Riemannian kernel function is represented by:

$$\kappa_{logE}(\hat{L}_{s_1,\gamma}, \hat{L}_{s_2,\gamma}) = \exp\left(-\frac{d^2_{logE}(\hat{L}_{s_1,\gamma}, \hat{L}_{s_2,\gamma})}{\sigma^2}\right),$$

wherein $s_1$ and $s_2$ represent two separate matrices of the plurality of symmetric positive definite matrices.

7. A computer-implemented method for diagnosing a medical image, the method comprising:
obtaining a medical image to be diagnosed;
obtaining a plurality of functional correlation matrices based on at least the medical image;
mapping the plurality of functional correlation matrices to a space of symmetric positive definite matrices to form a Riemannian manifold corresponding to a Riemannian kernel function;
obtaining a kernel-function matrix by using at least a principal component analysis to calculate one or more inner products of the mapped plurality of matrices based on at least the Riemannian kernel function;
calculating a first group of eigenvectors of the kernel-function matrix, the first group of eigenvectors including a first number of eigenvectors;
selecting one or more eigenvectors from the first group of eigenvectors to obtain a second group of eigenvectors, the second group of eigenvectors including a second number of eigenvectors;
wherein the second number is less than the first number; and
obtaining a diagnostic result associated with the medical image by at least inputting the second group of eigenvectors and a second group of eigenvalues corresponding to the second group of eigenvectors respectively into one or more classifiers.

8. The computer-implemented method of claim 7, wherein:
the obtaining a medical image to be diagnosed includes obtaining a functional magnetic resonance image;
the obtaining a plurality of functional correlation matrices based on at least the medical image includes:
obtaining a plurality of image data by at least performing one or more slice-time corrections, one or more head-motion corrections, one or more normalizations, one or more spatial filterings, and one or more temporal filterings on the medical image;
mapping the plurality of image data to multiple regions by at least dividing the plurality of image data into multiple sets of data, the multiple sets of date corresponding to the multiple regions respectively; and
obtaining the plurality of functional correlation matrices by at least calculating one or more correlation coefficients between the multiple sets of data.

9. The computer-implemented method of claim 7, wherein:
the first group of eigenvectors correspond to a first group of eigenvalues respectively; and
the second group of eigenvectors correspond to the second group of eigenvalues respectively.

10. The computer-implemented method of claim 9, wherein:
the first group of eigenvalues include a third number of eigenvalues; and
the second group of eigenvalues include a fourth number of eigenvalues;
wherein:
the third number is equal to the first number;
the fourth number is equal to the second number; and
the fourth number is less than the third number.

11. The computer-implemented method of claim 9, wherein the selecting one or more eigenvectors from the first group of eigenvectors to obtain a second group of eigenvectors includes:
selecting one or more eigenvectors from the first group of eigenvectors based on at least the first group of eigenvalues.

12. The computer-implemented method of claim 7, wherein the mapping the plurality of to-be-processed matrices to a space of symmetric positive definite matrices to form a Riemannian manifold corresponding to a Riemannian kernel function includes:
transforming the plurality of to-be-processed matrices to a plurality of semi-positive definite Laplacian matrices respectively:

$L_s = D_s - W_s$ wherein s is an integer variable ranging from 1 to S, S represents a total number of matrices for the plurality of to-be-processed matrices, $L_s$ represents each of the plurality of semi-positive definite Laplacian matrices, $D_s$ represents a degree matrix of each of the plurality of to-be-processed matrices, and $W_s$ represents each of the plurality of to-be-processed matrices; and
regularizing the plurality of semi-positive definite Laplacian matrices into a plurality of symmetric positive definite matrices respectively:

$\hat{L}_{s,\gamma} = L_s + \gamma I$ wherein $\hat{L}_{s,\gamma}$ represents each of the plurality of symmetric positive definite matrices, γ represents a positive integer, and I represents an identity matrix.

13. The computer-implemented method of claim 12, wherein the Riemannian kernel function is represented by:

$$\kappa_{logE}(\hat{L}_{s_1,\gamma}, \hat{L}_{s_2,\gamma}) = \exp\left(-\frac{d_{logE}^2(\hat{L}_{s_1,\gamma}, \hat{L}_{s_2,\gamma})}{\sigma^2}\right),$$

wherein $s_1$ and $s_2$ represent two separate matrices of the plurality of symmetric positive definite matrices.

14. A non-transitory computer-readable medium with instructions stored thereon, that when executed by a processor, perform the processes comprising:
obtaining a medical image to be diagnosed;
obtaining a plurality of functional correlation matrices based on at least the medical image;
mapping the plurality of functional correlation matrices to a space of symmetric positive definite matrices to form a Riemannian manifold corresponding to a Riemannian kernel function;
obtaining a kernel-function matrix by using at least a principal component analysis to calculate one or more inner products of the mapped plurality of matrices based on at least the Riemannian kernel function;
calculating a first group of eigenvectors of the kernel-function matrix, the first group of eigenvectors including a first number of eigenvectors;
selecting one or more eigenvectors from the first group of eigenvectors to obtain a second group of eigenvectors, the second group of eigenvectors including a second number of eigenvectors;
wherein the second number is less than the first number; and
obtaining a diagnostic result associated with the medical image by at least inputting the second group of eigenvectors and a second group of eigenvalues corresponding to the second group of eigenvectors respectively into one or more classifiers.

15. The non-transitory computer-readable medium of claim 14, wherein:

the obtaining a medical image to be diagnosed includes obtaining a functional magnetic resonance image;

the obtaining a plurality of functional correlation matrices based on at least the medical image includes:

obtaining a plurality of image data by at least performing one or more slice-time corrections, one or more head-motion corrections, one or more normalizations, one or more spatial filterings, and one or more temporal filterings on the medical image;

mapping the plurality of image data to multiple regions by at least dividing the plurality of image data into multiple sets of data, the multiple sets of date corresponding to the multiple regions respectively; and obtaining the plurality of functional correlation matrices by at least calculating one or more correlation coefficients between the multiple sets of data.

16. The non-transitory computer-readable medium of claim 14, wherein:

the first group of eigenvectors correspond to a first group of eigenvalues respectively; and the second group of eigenvectors correspond to the second group of eigenvalues respectively.

17. The non-transitory computer-readable medium of claim 16, wherein:

the first group of eigenvalues include a third number of eigenvalues; and the second group of eigenvalues include a fourth number of eigenvalues;

wherein:

the third number is equal to the first number;

the fourth number is equal to the second number; and the fourth number is less than the third number.

18. The non-transitory computer-readable medium of claim 16, wherein:

wherein the selecting one or more eigenvectors from the first group of eigenvectors to obtain a second group of eigenvectors includes:

selecting one or more eigenvectors from the first group of eigenvectors based on at least the first group of eigenvalues.

19. The non-transitory computer-readable medium of claim 14, wherein the mapping the plurality of to-be-processed matrices to a space of symmetric positive definite matrices to form a Riemannian manifold corresponding to a Riemannian kernel function includes:

transforming the plurality of to-be-processed matrices to a plurality of semi-positive definite Laplacian matrices respectively:

$$L_s = D_s - W_s$$

wherein s is an integer variable ranging from 1 to S, S represents a total number of matrices for the plurality of to-be-processed matrices, $L_s$ represents each of the plurality of semi-positive definite Laplacian matrices, $D_s$ represents a degree matrix of each of the plurality of to-be-processed matrices, and $W_s$ represents each of the plurality of to-be-processed matrices; and regularizing the plurality of semi-positive definite Laplacian matrices into a plurality of symmetric positive definite matrices respectively:

$$\hat{L}_{s,\gamma} = L_s + \gamma I$$

wherein $\hat{L}_{s,\gamma}$ represents each of the plurality of symmetric positive definite matrices, $\gamma$ represents a positive integer, and I represents an identity matrix.

20. The non-transitory computer-readable medium of claim 19, wherein the Riemannian kernel function is represented by:

$$\kappa_{logE}(\hat{L}_{s_1,\gamma}, \hat{L}_{s_2,\gamma}) = \exp\left(-\frac{d_{logE}^2(\hat{L}_{s_1,\gamma}, \hat{L}_{s_2,\gamma})}{\sigma^2}\right),$$

wherein $s_1$ and $s_2$ represent two separate matrices of the plurality of symmetric positive definite matrices.

* * * * *